(12) United States Patent
Jones et al.

(10) Patent No.: US 10,589,032 B2
(45) Date of Patent: Mar. 17, 2020

(54) DISPLAY ARRANGEMENT FOR AN INJECTION DEVICE

(71) Applicant: Sanofi, Paris (FR)

(72) Inventors: Matthew Jones, Warwick (GB); Anthony Paul Morris, Coventry (GB); Aled Meredydd James, Dorridge (GB); Paul Roger Griffin, Worcestershire (GB)

(73) Assignee: Sanofi, Paris (FR)

( * ) Notice: Subject to any disclaimer, the term of this patent is extended or adjusted under 35 U.S.C. 154(b) by 263 days.

(21) Appl. No.: 15/306,133

(22) PCT Filed: May 26, 2015

(86) PCT No.: PCT/EP2015/061542
§ 371 (c)(1),
(2) Date: Oct. 24, 2016

(87) PCT Pub. No.: WO2015/181141
PCT Pub. Date: Dec. 3, 2015

(65) Prior Publication Data
US 2017/0043097 A1    Feb. 16, 2017

(30) Foreign Application Priority Data

May 26, 2014    (EP) .................................... 14305778

(51) Int. Cl.
*A61M 5/315*    (2006.01)
*A61M 5/24*    (2006.01)
(Continued)

(52) U.S. Cl.
CPC .......... *A61M 5/31553* (2013.01); *A61M 5/24* (2013.01); *A61M 5/31541* (2013.01);
(Continued)

(58) Field of Classification Search
None
See application file for complete search history.

(56) References Cited

U.S. PATENT DOCUMENTS

| 3,069,083 | A |   | 12/1962 | Haydon |
| 5,279,586 | A | * | 1/1994  | Balkwill ............. A61M 5/3158 222/309 |

(Continued)

FOREIGN PATENT DOCUMENTS

| DE | 102004063652 | 7/2006 |
| EP | 0897728      | 2/1999 |
| EP | 2123317      | 11/2009 |

OTHER PUBLICATIONS

International Preliminary Report on Patentability in International Application No. PCT/EP2015/061542, dated Nov. 29, 2016, 8 pages.

(Continued)

*Primary Examiner* — Bhisma Mehta
*Assistant Examiner* — Matthew A Engel
(74) *Attorney, Agent, or Firm* — Fish & Richardson P.C.

(57) ABSTRACT

The present invention relates to a display arrangement for an injection device for displaying the size of a dose of a medicament, the display arrangement comprising:
- a housing (60) providing a rotation axis (3) extending in an axial direction (4),
- a first display member (22) rotatably supported inside the housing (60) with regard to the rotation axis (3) and having at least one cam (32) radially offset from the rotation axis (3),
- a second display member (24) rotatably supported inside the housing (60) with regard to the rotation axis (3) and arranged axially adjacent to the first display member (24), (Continued)

a coupling member (26) rotatably engaged with the second display member (24), wherein the coupling member (26) is engaged with the at least one cam (32) of the first display member (22) when the first display member (22) is in a predefined angular position or angular range, wherein the coupling member (26) and the first display member (22) are mutually engaged via a retaining arrangement (48) when the cam (32) and the coupling member (26) are disengaged.

19 Claims, 10 Drawing Sheets

(51) Int. Cl.
    *G06M 1/14*     (2006.01)
    *A61M 5/31*     (2006.01)

(52) U.S. Cl.
    CPC ........ *A61M 5/31585* (2013.01); *G06M 1/143* (2013.01); *A61M 2005/3126* (2013.01); *A61M 2205/581* (2013.01)

(56) References Cited

U.S. PATENT DOCUMENTS

| | | | | |
|---|---|---|---|---|
| 5,921,966 A * | 7/1999 | Bendek | ................... | A61M 5/24 604/207 |
| 8,202,255 B2 * | 6/2012 | Saiki | ................. | A61M 5/31551 604/181 |
| 8,298,194 B2 * | 10/2012 | Moller | ................... | A61M 5/24 604/181 |
| RE43,834 E * | 11/2012 | Steenfeldt-Jensen | ....................... | A61M 5/31551 604/207 |
| 8,372,042 B2 * | 2/2013 | Wieselblad | ....... | A61M 5/31525 604/186 |
| 8,617,124 B2 * | 12/2013 | Wieselblad | ............. | A61M 5/20 604/189 |
| 9,452,266 B2 * | 9/2016 | Roervig | ................... | A61M 5/24 |
| 2005/0137571 A1 * | 6/2005 | Hommann | ......... | A61M 5/31553 604/500 |
| 2007/0016142 A1 * | 1/2007 | Burren | ..................... | A61M 5/24 604/207 |
| 2007/0233015 A1 * | 10/2007 | Saiki | ................. | A61M 5/31551 604/207 |
| 2008/0183139 A1 * | 7/2008 | Burren | ............. | A61M 5/31553 604/211 |
| 2012/0010575 A1 * | 1/2012 | Jones | ................ | A61M 5/31555 604/211 |
| 2012/0296276 A1 * | 11/2012 | Nicholls | ........... | A61M 5/31501 604/110 |
| 2016/0051768 A1 * | 2/2016 | Butler | ..................... | A61M 5/20 604/211 |
| 2016/0051769 A1 * | 2/2016 | Jones | ..................... | A61M 5/20 604/211 |
| 2016/0051770 A1 * | 2/2016 | Jones | ..................... | A61M 5/20 604/211 |

OTHER PUBLICATIONS

International Search Report and Written Opinion in International Application No. PCT/EP2015/0615542, dated Oct. 8, 2015, 11 pages.

* cited by examiner

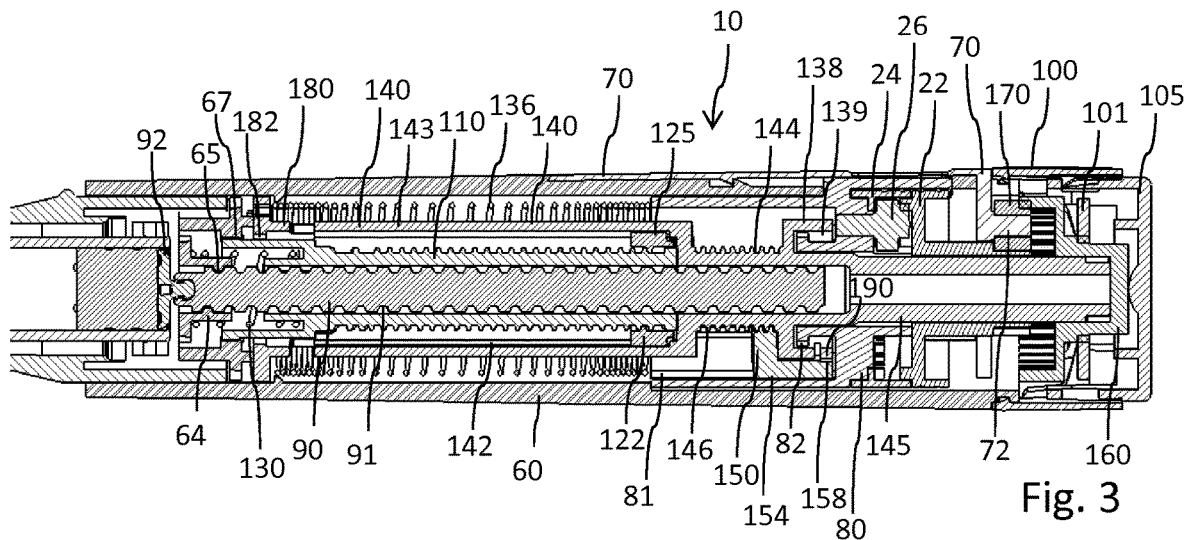
Fig. 3
Fig. 4
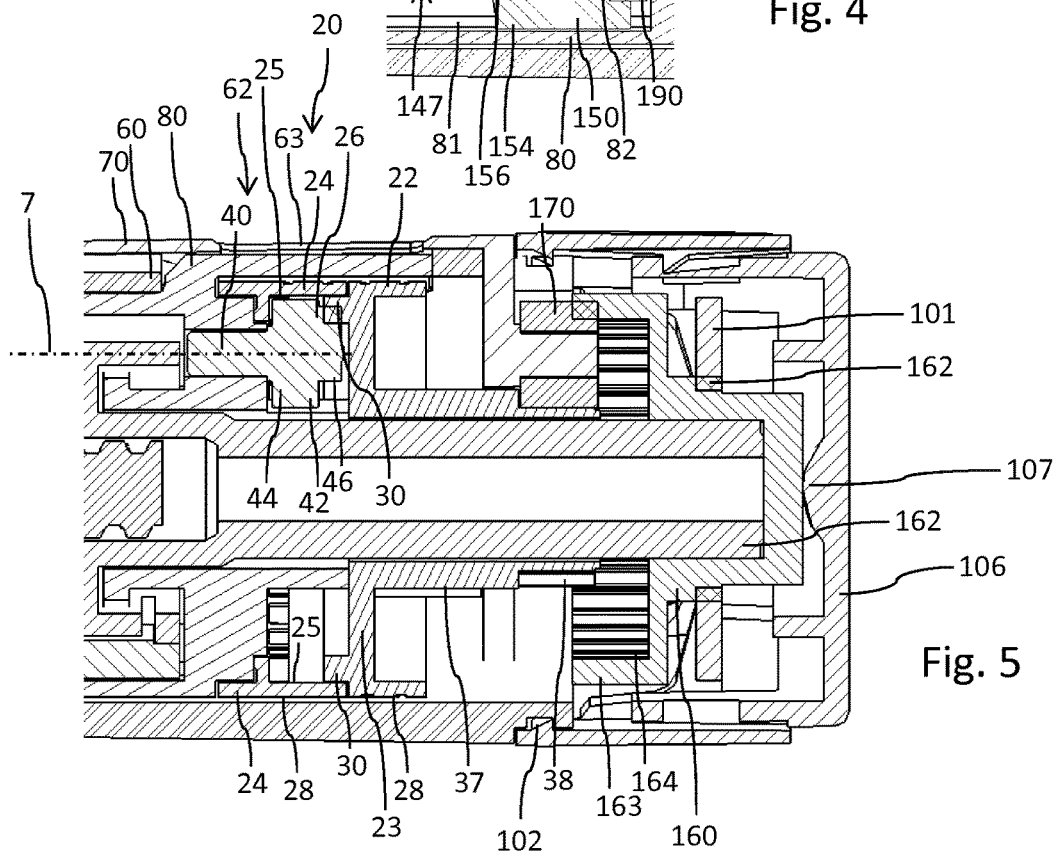
Fig. 5

DISPLAY ARRANGEMENT FOR AN INJECTION DEVICE

CROSS-REFERENCE TO RELATED APPLICATIONS

This application is a U.S. national stage application under 35 USC § 371of International Application No. PCT/EP2015/061542, filed on May 26, 2015, which claims priority to European Patent Application No. 14305778.4 filed on May 26, 2014, the entire contents of which are incorporated herein by reference.

TECHNICAL FIELD

The present invention relates to a display arrangement for an injection device, to a drive mechanism and to a respective injection device. In particular, the invention relates to an injection device such like a pen-type injector inter alia comprising an odometer like display arrangement to visualize the size of a dose actually set by a user of the device.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be entirely discarded when the medicament in the cartridge has been completely dispensed or used-up.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be entirely discarded when the medicament in the cartridge has been completely dispensed or used-up.

Injection devices such like pen type injectors also provide a dose indicating mechanism which is operable to display the size of a set dose to a user. Typically, the housing of such injection devices comprises a dose indicating window where a number representing the size of the dose shows up.

Especially with elderly or visually impaired patients, reading of such dose indicating numbers is sometimes difficult. With devices adapted for injection of e.g. insulin, typical dose sizes may vary between 0 and 120 IU (International Units) of insulin. Due to the rather compact design and limited geometrical dimensions of such injection devices the size of such dose indicating numbers is fairly small. For visually impaired persons reading of such tiny numbers may therefore be rather difficult. Known display arrangements of such injection devices are only able to show even numbers or only some discrete numbers between 0 and 120. However, since such injection devices are intended for self-medication treatment, it is of importance, that the user is able to correctly determine the size of dose actually set.

SUMMARY

Some aspects of the present disclosure can be implemented to avoid disadvantages of known injection devices and display arrangements thereof and to provide an improved display arrangement for an injection device allowing for an intuitive operation, both for setting and for dispensing of a dose. It is intended to provide a display arrangement that is operable to continuously visualize all available discrete dose sizes that can be set and subsequently dispensed with the device. In addition, the display arrangement should be easy and unequivocal to read even for persons suffering impaired vision.

Some aspects can also be implemented to provide a drive mechanism for a drug delivery cooperating with the display arrangement and being operable to set and to dispense a dose of a medicament.

Some aspects can also be implemented to provide an injection device comprising such a drive mechanism and comprising a cartridge sealed with a piston and being operably engaged with a piston rod of such drive mechanism.

In a first aspect the invention relates to a display arrangement for an injection device, which display arrangement is operable and configured to display the size of a dose of a medicament to be delivered or to be dispensed by the injection device. The display arrangement comprises a housing providing a rotation axis that extends in an axial direction. In other words, the housing due to its inner or outer geometry defines a longitudinal or axial direction which may coincide with the rotation axis. The rotation axis does not have to be physically or structurally implemented in the housing in terms of a centrally located bearing. The rotation axis may define a virtual axis that extends through the center of the housing and which defines a kind of a symmetry axis in regard of which numerous components of the display arrangement or of the injection device may rotate relative to the housing.

The display arrangement further comprises a first display member rotatably supported inside the housing with regard to the rotation axis. The first display member has at least one cam or tappet radially offset from the rotation axis. Hence, the cam is located radially offset from a radial center of the display member. The cam or tappet may be located at an outer radial edge or border region of the rotatable display member.

The display arrangement further comprises a second display member rotatably supported inside the housing with regard to the rotation axis. The second display member is arranged axially adjacent to the first display member. The second display member may axially abut with the first display member. First and second display members are typically designed and configured to display different digits of a two or three digit number. While the first display member may be provided with integer numerals 0, 1, 2, . . . , 9 the second display member may be provided with numerals 1, 2, 3, . . . , 12, representing decades or tens while the numerals of the first display member represent the ones of an at least two digit number. The first display member therefore represents one digit and the second display member may represent a second and/or a third digit of a two- or three-digit number.

By making use of two display members each being rotatably supported inside the housing every integer and discrete number within a large dose size interval can be visualized by means of the display arrangement. In this way, the overall precision and legibility of the display arrangement can be improved, so that even visually impaired persons become enabled to unequivocally read the dose size information represented by first and second display members. Furthermore, by making use of two separate display members, the size of the digits represented by each display member can be increased to a maximum, thereby supporting a good, unequivocal and intuitive legibility and readability of the dose size information.

The display arrangement further comprises a coupling member rotatably engaged with the second display member and selectively engageable with the at least one cam of the first display member. Typically, the coupling member is permanently rotatably engaged or rotatably fixed with the second display member, so that any rotation of the coupling member is transferred to a respective rotation of the second display member. The selective engagement between the coupling member and the at least one cam of the first display member provides a kind of a counter mechanism.

The cam only selectively engages with the coupling member depending on the angular position or angular range of the first display member. Since the cam is arranged radially offset from the rotation axis it is operable to only temporarily, hence to selectively, engage with the coupling member being also located at a respective radial distance from the first and second display member's rotation axis. While the position of the coupling member may be fixed the cam rotates with the first display member so that the cam only engages with the coupling member when the first display member is at a predefined angular position or within a predefined angular range during a rotation or during complete revolution of the first display member.

If the first display member comprises only one cam it engages only once with the coupling member during a complete revolution. Having two cams on the first display member there will be two consecutive engagements between the first display member and the coupling member during a complete revolution of the first display member. When having several cams the cams are typically equidistantly distributed along the outer circumference of the first display member. Any time a cam engages with the coupling member or passes by the coupling member during a rotation or revolution of the first display member, the coupling member is triggered or driven to move or to rotate a predefined distance or angular range so that the second display member rotates a well-defined discrete step.

When the cam has passed the coupling member during a revolution or rotation of the first display member, the cam and first display member are no longer coupled. They are effectively disengaged so that a further rotation of the first display member has no effect on the coupling member nor on the second display member. It is only when the at least one cam repeatedly engages with the coupling member that the coupling member and hence the second display member is driven one discrete and well-defined step further.

The display arrangement further comprises a retaining arrangement by way of which the coupling member and the first display member are mutually engaged. The retaining arrangement may permanently engage coupling member and first display member and may allow and support a movement or rotation of the coupling member by the first display member only when the first display member is in the predefined angular position or in the predefined angular range. When the first display member is outside the predefined angular position or outside the predefined angular range the retaining arrangement serves to prevent a self-actuated or otherwise triggered movement or rotation of the coupling member. In this way and by means of the retaining arrangement a self-actuated or unintentional rotation of the second display member can be counteracted and prevented when cam and coupling member are disengaged.

By implementing a retaining arrangement directly acting between the coupling member and the first display member the implementation of a retaining means, such like ratchets, by way of which the second display member may for instance be coupled to the housing becomes superfluous. Providing a retaining arrangement between the coupling member and the first display member is also beneficial for a smooth and well-defined rotation of the second display member. Thanks to the retaining arrangement mutually engaging the coupling member and the first display member the second display member is fixable relative to the housing when cam and coupling member are disengaged. In this way a mutual interaction and coupling between the second display member and the housing, e.g. in form of a ratchet mechanism, can be circumvented. In effect, a minimum driving force or angular momentum necessary to rotate the second display member at least one step further can be advantageously reduced, since rotation or displacement of the coupling member does not require to act against a restoring or retaining force acting between the housing and second display member.

It is further to be mentioned here, that the coupling member rotatably engaged with the second display member may be also provided as a separate piece that may be rotatable or displaceable relative to the second display member. However, there are embodiments conceivable, in which the coupling member and the second display member are permanently engaged or mutually fixed. The coupling member may even be designed as an integral portion of the second display member. Hence, any reference to the coupling member may also be interpreted as a reference to a portion or section of the second display member.

According to an embodiment the retaining arrangement is configured to keep the coupling member in a fixed angular position while the first display member is rotatable between consecutive predefined angular positions or predefined angular ranges. Only in predefined angular positions or predefined angular ranges its cam engages with the coupling member during a revolution of the first display member. In such configurations the retaining arrangement may allow and support a displacement, typically a rotation of the coupling member, driven by the displacement of the cam.

In other words, when the cam engages with the coupling member the retaining arrangement is temporarily deactivatable thereby allowing and/or supporting a rotation or displacement of the coupling member to rotate the second display member at least one step further. In all angular positions of the first display member located between the predefined angular position or positions or predefined angular range or ranges the retaining arrangement is active and is engaged with the coupling member in such a way, that it prevents any further displacement or rotation thereof.

Typically, the retaining arrangement and the engagement of cam and coupling member are alternately activatable and deactivatable. When the cam and the coupling member mutually engage the retaining arrangement is substantially inactive so that the coupling member and the second display member can be displaced or rotated. If the cam and the coupling member are disengaged the retaining arrangement is active and engages with the coupling member and hence with the second display member in order to prevent any further rotation thereof even when the first display member is actually subject to a further rotation.

As seen from the perspective of the coupling member, the coupling member is either engaged with the cam of the first display member or the coupling member is engaged with the retaining arrangement.

According to another embodiment the coupling member is rotatably supported in the housing with regard to a coupling axis that extends parallel but radially offset to the rotation axis. By implementing the coupling member as a rotatable coupling member, the angular displacement of the cam and the cam's bypassing of the coupling member serves to induce a rotation of the coupling member, which is directly transferable into a respective rotative movement of the second display member. The parallel orientation of the coupling member's coupling or rotation axis to the rotation axis of first and second display members is beneficial to transfer a torque from the first display member via the coupling member to the second display member, typically for driving the second display member at least one discrete step further. In various embodiments By arranging the coupling member radially offset to the rotation axis the coupling member is selectively engageable with the cam whose position radially offset from the rotation axis corresponds to the coupling member's radial offset or distance from the rotation axis. Typically, the radial distances of the cam and the coupling member slightly differ to such an extent that the cam is enabled to pass by the coupling member during a revolution of the first display member. The cam may be arranged at such a radial distance from the rotation axis that it either engages with a radially inwardly-facing portion of the coupling member or with a radially outwardly-facing portion of the coupling member. The active and engaging portion of the cam always faces towards the coupling member. The engaging portion of the cam therefore faces either radially outwardly or radially inwardly.

The size and position of the coupling member relative to the first display member defines the predefined angular position or predefined angular range at which the cam operably engages with the coupling member.

The geometric size and extension of the coupling member defines the size of the angular range across which the cam is in engagement with the coupling member during a revolution of the first display member.

According to another embodiment the coupling member comprises a first geared section with numerous first teeth to mesh with the cam when the first display member is in the predefined angular position or in the predefined angular range. By having a first geared section extending in a plane perpendicular to the rotation axis and/or to the coupling axis the cam is selectively engageable with the coupling member when passing by the coupling member. By means of the first geared section with a number of equidistantly and radially outwardly extending teeth a positive engagement between cam and coupling member can be at least temporarily established when the cam engages with the coupling member. In this way, a slip-free engagement and transfer of a respective driving torque from the cam and hence from the first display member to the coupling member and hence to the second display member can be provided.

In another embodiment at least one of first display member and second display member comprises a sleeve-like shape and further comprises a display surface on its outer circumference provided with consecutive dose size indicating symbols. Typically, both, first and second display members comprise a display sleeve each of which having a display surface with a sequence of numbers. The dose size indicating symbols typically comprise consecutive numbers. Here, the first display member may be provided with the ones digit of a two or three digit number. On the display surface of the first display member there may be arranged a sequence of ten digits or numbers 0, 1, 2, . . . , 9. The second display member, may represent the decades or tens of a two or three digit number. For displaying numbers like 10, 20, 30, . . . , 120 the second display member comprises a sequence of digit ranges such like 0, 1, 2, . . . , 12. In this way and by means of first and second display members arranged axially adjacent and substantially co-radial every integer number e.g. between 0 and 120, can be precisely displayed in a window or aperture of the housing that provides a partial view of both, first and second display members. First and second display members axially flush along their outer circumference.

Typically, first and second display members may comprise a sleeve-like or ring-like shape. Their outer radius typically corresponds with the inner radius of the tubular housing. The outer radius of first and second display members is slightly smaller than the inner radius of the housing so as to permit a smooth rotation of first and second display members inside the housing. By maximizing the diameter of first and second display members so that first and second display members just fit into the interior of the housing the overall size of a display surface thereof can be maximized. Consequently, also the size of the symbols or numbers presented and provided on respective display surfaces can be increased, thereby providing a good, intuitive and unequivocal legibility thereof.

The aperture or window provided in the housing may be covered or provided with a magnifying cover, such like a magnifying lens, by way of which the visual appearance of the symbols provided on display surfaces of first and second display members can be further increased. In this way, the legibility of a dose size represented by the angular positions of first and second display members can be further improved.

According to another embodiment the coupling member comprises a second geared section with numerous second teeth meshing with a geared section of the second display member. Typically, first and second geared sections of the coupling member are axially offset. Hence, they may be separated from each other in axial direction. An axial distance between first and second geared sections of the coupling member may correspond to the axial distance of first and second display members. It may typically correspond and may be substantially equal to the axial distance between the first display member's cam, selectively engaging with the first geared section and with the second display member's geared section, permanently engaged with the second geared section of the coupling member.

First and second geared sections of the coupling member may be integrally or unitarily formed. First and second geared sections can be fixed with respect to each other. First and second geared section of the coupling member may have a substantially equal shape and geometry. Depending on a required transmission or gear ratio the size, the geometry as well as the number of teeth of first and second geared sections of the coupling member may also vary. In particular, the geometry and number of teeth of the first geared section may differ from the geometry and number of teeth of the second geared section of the coupling member. It is also conceivable, that first and second geared sections have identical geometries and are positioned flush in the axial direction.

Insofar, first teeth and second teeth of the first and second geared section of the coupling member may be considered as first and second axial portions of a common and a single geared section of the coupling member.

There are also embodiments conceivable, wherein first and second geared sections of the coupling member are separated by a separating disc extending tangentially and radially between consecutive teeth of the coupling member's first and second geared sections. By means of such a separating disc, axial support can be provided e.g. for the second display member, in particular for a geared section thereof meshing with the second teeth of the coupling member's second geared section. The separating disc may be further of benefit for and during assembly if the display arrangement or of the injection device.

By means of the second geared section the coupling member is permanently rotatably engaged with the second display member. By means of teeth and geared sections that mutually mesh a positive engagement between the coupling member and the second display member is attainable, thereby providing a slip-free transfer of a driving torque to the second display member.

According to a further embodiment the retaining arrangement comprises at least two retaining teeth separated in the circumferential direction on the outer circumference of the coupling member. The retaining arrangement further comprises a retaining ring provided on the first display member. The retaining teeth of the retaining arrangement are in radial abutment with the retaining ring when the first display member and hence its cam is located outside the predefined angular position or predefined angular range. The geometry and angular separation of the at least two retaining teeth is selected such that both teeth radially engage or radially abut with a radially inwardly-facing portion of the retaining ring of the first display member.

For this, retaining teeth and retaining ring axially overlap. Since both retaining teeth are simultaneously in engagement and abutment with the retaining ring, a rotation of the retaining ring, hence a rotation of the respective first display member is not transferable to a rotation of the retaining teeth. Typically, the retaining teeth engage with a side flank or with a side edge with the radially inwardly-facing and substantially flat and even-shaped sidewall portion of the retaining ring. Depending on the circumferential separation of retaining teeth and their respective angular orientation, that arises from their radially outwardly-directed extension, the retaining teeth, in particular the tips of the retaining teeth may be somewhat bevelled to form respective side flanks to abut to a large extent the inward-facing sidewall portion of the retaining ring. In this way, the retaining ring and hence the first display member may smoothly slide along the side flanks of the at least two retaining teeth of the coupling member, while keeping the coupling member rotatably fixed.

Typically, the coupling member comprises at least three equidistantly arranged retaining teeth along the outer circumference of the coupling member. Consequently, consecutive teeth may be separated by 120°. In this way and when the first display member is outside the predefined angular position or angular range always two retaining teeth are in direct engagement with the retaining ring while the third retaining tooth and the retaining ring are substantially disengaged. When the cam engages with the coupling member the coupling member experiences a rotation and the third retaining tooth may get in engagement and abutment with the retaining ring while a first retaining tooth may liberate and disengage from the retaining ring.

According to a further embodiment the retaining teeth are arranged axially offset and/or axially adjacent to the coupling member's first teeth. Hence, the retaining teeth, which may form a retaining section or a third geared section of the coupling member are located in a plane perpendicular to the rotation axis or perpendicular to the coupling axis, which retaining plane is axially offset from the plane, in which the first geared section of the coupling member is located. In this way, the cam of the first display member may exclusively engage with the first geared section of the coupling member when arriving at the predefined angular position or when entering the predefined angular range. Consequently, the cam of the first display member is substantially free of interaction with the coupling member's retaining teeth or retaining section.

According to another embodiment the retaining teeth's radial extension is shorter than the first teeth's radial extension. In this way, the cam may axially extend across the retaining teeth without getting in contact with the retaining teeth but to selectively engage with the first geared section and its first teeth. Due to the shorter radial extension of the retaining teeth, the retaining teeth are and remain radially collision less with regard to the cam. Even though the cam may axially overlap with the retaining section and hence with the retaining teeth of the coupling member, the radially shortened retaining teeth are hindered from interacting or from engaging radially with the cam.

According to a further embodiment the retaining teeth are at least in sections axially flush with at least two of the first teeth. It is of particular benefit, when the retaining teeth are located at an angular position that substantially overlaps with the angular position of selected first teeth of the first geared section of the coupling member. It is particularly conceivable, that the number of first teeth is larger than the number of retaining teeth. Hence, the number of the first teeth may be two times the number of retaining teeth. For instance, there may be provided six first teeth but only three retaining teeth. It is then of particular benefit, when every second tooth of the first teeth is axially extended by a radially stepped down retaining tooth. In general already three retaining teeth are sufficient to provide and to establish the retaining arrangement. Numerous and a larger number of first teeth is generally beneficial for a selective and well-defined, smooth engagement of cam and coupling member.

According to a further embodiment the cam radially overlaps with the retaining ring but axially protrudes from the retaining ring. Typically, the retaining ring may also axially protrude from a solid body portion of the first display member. Hence, the retaining ring forms an annular rim at or near the outer circumference of the disc or sleeve-shaped first display member. The coupling member's retaining section with the retaining teeth axially coincides with the retaining ring while the cam as well as the first geared section of the coupling member are arranged axially adjacent thereto or axially offset therefrom.

In this way a rather compact and small sized overall design and structure of the display arrangement can be obtained.

According to a further embodiment the retaining ring comprises a radially extending slit or recess to receive one of the retaining teeth when the first display member rotates through the predefined angular range or beyond the predefined angular position. Hence, when the cam of the first display member engages with the coupling member so as to rotate the coupling member by a discrete step, one of the retaining teeth is allowed to enter the retaining ring's slit or recess thereby disabling or temporarily deactivating the retaining arrangement. As the retaining tooth is allowed to radially enter the slit or recess the coupling member is rotatable as long as the other retaining teeth do not engage with or abut a radially inwardly-facing sidewall portion of the retaining ring that is circumferentially offset from the retaining ring's slit or recess. Typically, the slit or recess coincides with the angular position of the cam.

According to a further embodiment the cam comprises a first cam segment and a second cam segment separated in circumferential direction by the retaining ring's slit or recess extending therebetween in axial and radial direction. In this embodiment the cam is segmented in two cam segments that are separated by the retaining ring's slit or recess. In operation, each one of the cam segments is operable to engage with the first geared section of the coupling member. Typically, those portions of the cam segments facing away from each other in circumferential direction of the first display member comprise a somewhat symmetrical shape, so that a torque in both directions of rotations, hence a torque in dose incrementing direction as well as a torque in dose decrementing direction can be equally transferred to the coupling member and hence to the second display member.

The separation of the cam into two cam segments is also beneficial for the purpose of assembly of the display arrangement. In this way, the coupling member and the first display member can be assembled by means of a relative axial displacement.

The segmentation of the cam into first and second cam segments can also be interpreted that the retaining ring is interrupted by the slit or recess, wherein first and second cam segments are provided and arranged on opposite end portions of the interrupted retaining ring.

According to another aspect the invention further relates to a drive mechanism for an injection device for setting and dispensing of a dose of a medicament. The drive mechanism is typically user-operated. It may be semi-automated. It may be powered or driven by an energy storage element, typically by a mechanical energy storage element, such like a tension spring. However, the drive mechanism is generally not limited to such semi or fully automated drive mechanisms. The drive mechanism may also be implemented as a user-driven mechanism, wherein a dispensing force has to be completely provided by a user of the device. The injection device is particularly implemented as an auto-injector having an energy storage by way of which a driving or dispensing force or torque can be provided for the injection of a dose of a medicament.

The drive mechanism comprises an elongated housing extending in an axial direction. The drive mechanism further comprises a piston rod to operably engage with a piston of a cartridge. Mutual engagement of the piston rod and the cartridge's piston and displacement of the piston rod in axial distal direction displaces the piston correspondingly in axial distal direction so as to expel a predefined amount, hence a dose of the medicament from the cartridge. The drive mechanism further comprises a dose setting member rotatably supported on or in the housing allowing a user to individually set a dose of required size. By dialing or rotating the dose setting member a dose of respective size can be set, which in a subsequent step is dispensable by the drive mechanism. The rotation of the dose setting member defines the distance the piston rod advances in the distal direction during a consecutive dose dispensing procedure.

The drive mechanism further comprises a drive sleeve rotatably or threadedly engaged with the piston rod. The drive sleeve is operable to transfer a driving force or driving torque to the piston rod. The piston rod may either be threadedly engaged with the housing so that a rotation of the piston rod induced and driven by the drive sleeve leads to an axial displacement of the piston rod relative to the housing. In other embodiments it is conceivable that the piston rod is rotatably fixed but slidably supported inside and relative to the housing. Then, the drive sleeve may be axially constrained or axially fixed relative to the housing and may be threadedly engaged with the piston rod. A rotation of the drive sleeve will then equally serve to displace the piston rod in distal direction for the purpose of dose dispensing.

In addition, the drive mechanism comprises a display arrangement as described above. The display arrangement is alternately engageable with the drive sleeve, namely during dose dispensing and with the dose setting member, namely during dose setting. The display arrangement and its engagement with the dose setting member during and for setting of a dose provides information to a user about the size of the dose actually set. During a consecutive dose dispensing procedure the display arrangement is typically decoupled from the dose setting member, so that any further manipulation of the dose setting member has no influence on the dose size. A decoupling of the display arrangement from the dose setting member typically comes along with a coupling of the display arrangement with the drive sleeve. During dose dispensing the drive sleeve rotates in a dose decrementing direction so that the display arrangement returns into an initial configuration at the end of a dose dispensing procedure.

The elongated housing of the drive mechanism may coincide with the housing of the display arrangement. Hence, drive mechanism and display arrangement may be both arranged and positioned in a common housing. This housing may even form a proximal housing portion of the injection device. However, it is conceivable, that the display arrangement is implemented as a separate unit that may be attached and operably engaged with the drive mechanism and/or with the injection device in a modular manner. In such an embodiment the display arrangement may comprise a housing on its own.

According to another embodiment the drive mechanism comprises an arc-shaped clicking member to audibly engage with a toothed structure of the housing or of an insert attached to the housing. The clicking member is typically attached to the dial sleeve or is integrally formed therewith.

During dose dispensing the clicking member rotates relative to the housing or insert thereby generating an audible click sound as a tooth or nose portion thereof meshes with the toothed structure of the housing or insert. Moreover, the clicking member is elastically and radially deformable by engagement with an axially displaceable last dose limiting member.

The nose portion of the clicking member is provided at or near a free end of the arc shaped clicking member. Radially outwardly at a tangential or circumferential distance from this free the clicking member comprises a radially outwardly extending portion to engage with a radially inside facing portion of the single dose limiting member. As the single dose limiting member approaches an end of dose position at the end of a dose dispensing procedure it serves to displace and to bend the clicking member radially inwardly. In this way the effective free length of the clicking member is shortened and the acoustical properties thereof audibly change to indicate to a user that the end of the dosing procedure has been reached or will be reached soon. Hence, with only a single clicking member different and distinguishable clicking sounds can be generated.

In still another aspect the invention further relates to an injection device for dispensing of a dose of a medicament. The injection device at least comprises a display arrangement as described above.

In a further embodiment the injection device comprises a drive mechanism as described above and a cartridge at least partially filled with the medicament. The cartridge is typically arranged in the housing of the injection device or in the housing of the drive mechanism. It is also conceivable that the cartridge is arrangeable and located in a separate housing, denoted as cartridge holder, which is connected to the aforementioned housing or which is connectable to the housing. A releasable connection of cartridge holder and housing or body of the drive mechanism or injection device allows for cartridge replacement. The injection device is then designed and configured as a reusable device. Typically, the drive mechanism is then re-settable.

In other embodiments the cartridge holder is non-releasably connected to the housing in such a way, that cartridge holder and housing are only separable by a destruction of cartridge holder or housing. In such embodiments the injection device is typically designed as a disposable device having the cartridge readily disposed therein. After use of the medicament the entire device is intended to be discarded. Then, the drive mechanism is void of a reset feature. Typically, when reaching a last dose configuration, in which the piston rod reaches its most distal position the drive mechanism becomes substantially inoperable.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-630) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly -Thr-Phe-Thr-Ser-Asp-Leu-Ser-Lys-Gln-Met-Glu-Glu-Glu-Ala-Val-Arg-Leu-Phe-Ile-Glu-Trp-Leu -Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, an embodiment of the display arrangement, the drive mechanism and the injection device is described in detail by making reference to the drawings, in which:

FIG. 3 shows another longitudinal cross-section through the drive mechanism in an initial configuration, FIG. 4 is an enlarged cross-section of a dose limiting mechanism, FIG. 5 shows an enlarged longitudinal cross-section of the display arrangement.

DETAILED DESCRIPTION

Figure 1:
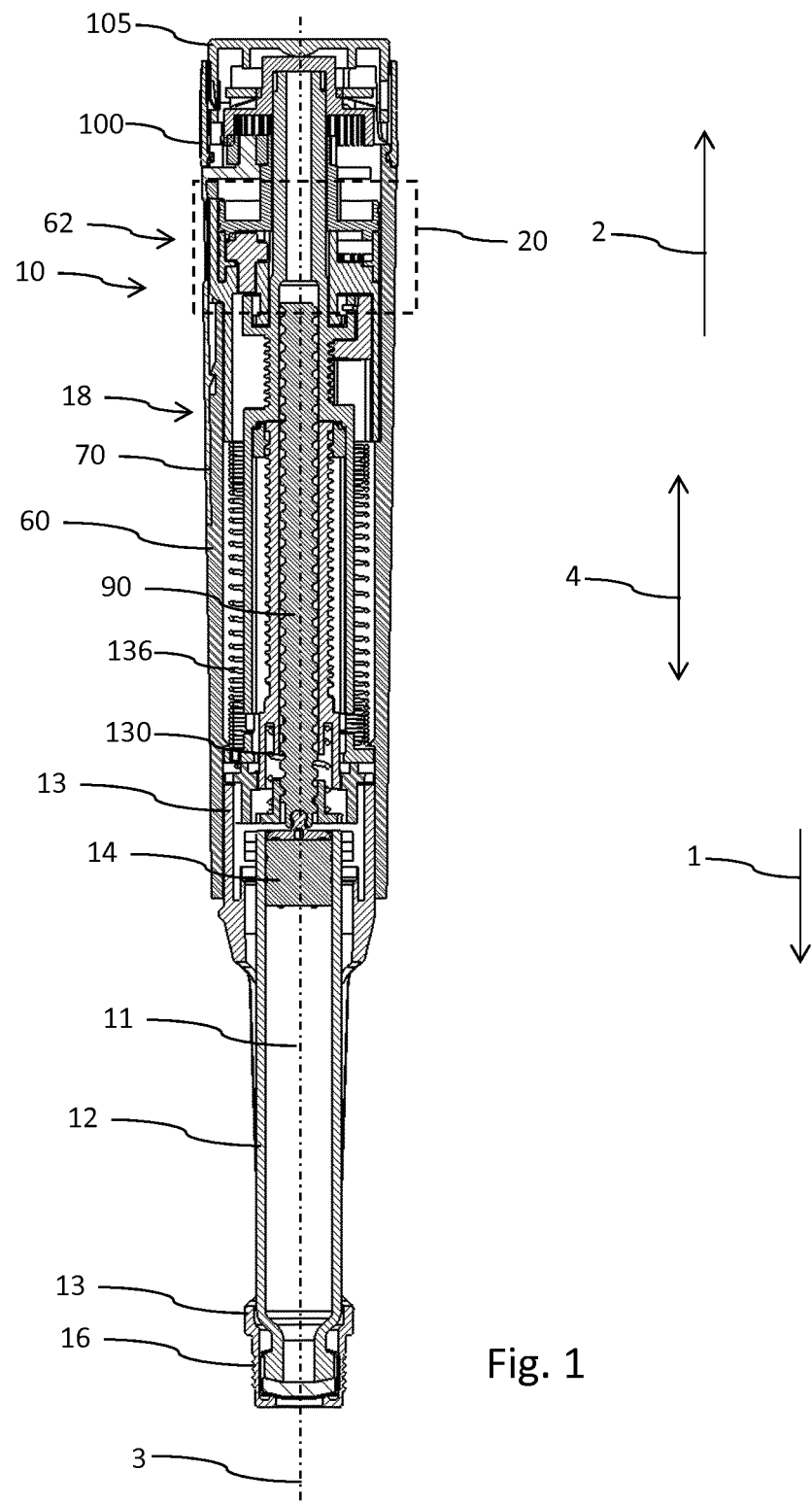
FIG. 1 shows a longitudinal cross-section through the injection device.
Figure 2:
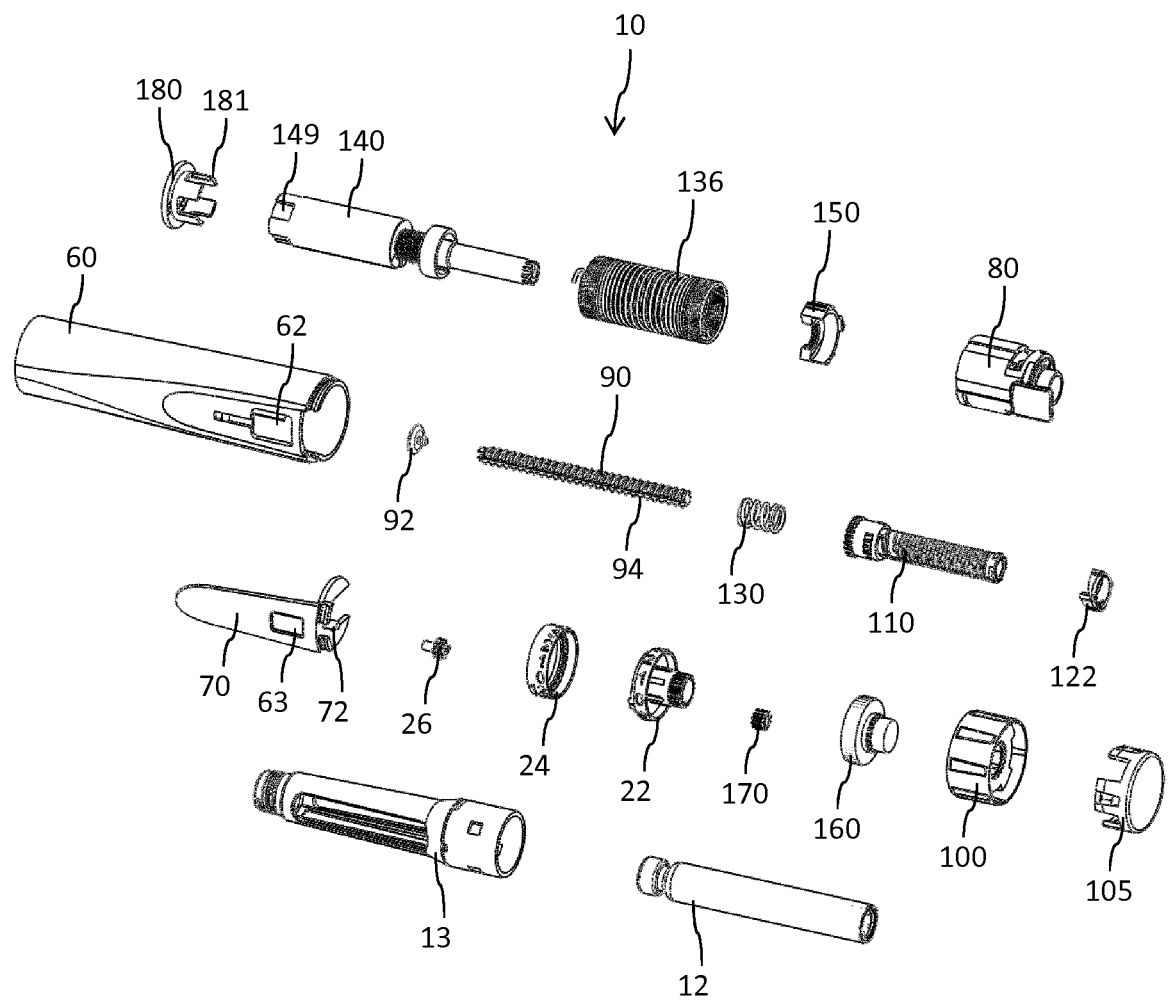
FIG. 2 shows an exploded and perspective view of the various components of the injection device.

In FIGS. 1 and 2, the complete injection device 10 is illustrated in a longitudinal cross section and in an exploded view with its various components. The injection device 10 is of pen-injector type and comprises a substantially cylindrical and axially elongated shape. Throughout the Figures the axial distal direction is denoted with reference number 1 and the opposite proximal direction is denoted with reference number 2. The injection device 10 comprises a drive mechanism 18 and further has a proximal housing 60, also denoted as body in which the drive mechanism 18 is accommodated. The housing 60 defines a longitudinal or axial direction 4 and further has at its centre a rotation axis 3, with regard to which various components of the injection device 10 are rotatable.

In distal direction 1 the housing 60 is connected with a cartridge holder 13 which is adapted to accommodate and to receive a cartridge 12 containing the medicament 11 to be dispensed by the injection device 10 by way of its drive mechanism 18. The cartridge 12 typically comprises a vitreous barrel of cylindrical or tubular shape and is sealed in distal direction 1 by a pierceable sealing member, such like a septum.

In proximal direction 2, the cartridge 12 is sealed by means of a piston 14 slidably arranged in the barrel of the cartridge 12. The piston 14 typically comprises an elastomeric material, by way of which the proximal end of the cartridge 12 can be effectively sealed in a fluid- and gas-tight manner. The piston 14 of the cartridge 12 is to be operably engaged with a distal end of a piston rod 90 of the injection device's 10 drive mechanism 18. A distally directed displacement of the piston 14 typically induced and governed by the piston rod 90 leads to a respective build up of a fluid pressure inside the cartridge 12. When the distal outlet of the cartridge 12 is connected with e.g. a needle assembly, which is not illustrated here, a predefined amount of the liquid medicament, which equals a previously set dose, can be expelled from the cartridge 12 and can be dispensed via the injection needle. At its distal end the injection device 10, hence the cartridge holder 13 thereof comprises a threaded socket 16 to releasably engage with the needle assembly.

The cartridge holder 13 and hence the cartridge 12 assembled therein is to be protected and covered by a removable protective cap, which is not further illustrated. Prior to setting and/or dispensing of a dose, the protective cap 19 of the injection device 10 as well as an inner needle cap of the needle assembly have to be removed. After dispensing or injecting of the medicament, e.g. into biological tissue, the needle assembly is typically to be disconnected from the cartridge holder 13 and is to be discarded.

The drive mechanism 18 as illustrated in the various FIGS. 1 to 20 comprises numerous functional and mechanically inter-engaging components by way of which a dose of variable size can be set and subsequently dispensed. The drive mechanism 18 is of semi-automated type. It comprises a means for storing mechanical energy during a dose setting procedure. Said mechanical energy is then usable for driving the piston rod in distal direction 1 during a dose dispensing procedure. Consequently, it is the device 10 and the drive mechanism 18 that provide mechanical energy and a driving force or driving torque to conduct an injection procedure. Consequently, an injection force does not have to be provided by the user during the dose dispensing process.

Dose dispensing requires distally directed advancing of the piston rod 90 relative to the cartridge 12, hence relative to the cartridge holder 13 and relative to the housing 60. The drive mechanism 18 is operable to set a dose of arbitrary size. The size of a dose actually set is visually displayed to a user via a display arrangement 20 located in a proximal portion of the housing 60. The housing 60 comprises a substantially cylindrical hollow shape. As shown in FIG. 2 it comprises a window 62 near its proximal end covered by an inlay 70.

The inlay 70 has a transparent cover 63 that overlaps with the window of the housing 60. The cover can include a magnifying lens so that numbers or symbols of display surfaces 28 of the display arrangement 20 appear enlarged to a user. In the instance illustrated in FIG. 3, the housing 60 near its distal end comprises a centrally-located threaded support 64 that receives the threaded piston rod 90. The axially elongated piston rod 90 comprises an outer thread 91 that is threadedly engaged with an inner thread 65 of the support 64. In this way, a rotation of the piston rod 90 relative to the housing 60 leads to a distally-directed advancing motion of the piston rod 90 relative to the housing 60 and relative to the barrel of the cartridge 12.

At its distal end the piston rod is rotatably connected with a radially widened pressure piece 92, which almost completely abuts with a proximal thrust-receiving surface of the cartridge's 12 piston 14. Due to the rotatable bearing of the pressure piece 92 on the piston rod 90, the pressure piece may rest on the piston 14 while the piston rod 90 rotates during dose dispensing.

Figure 17:
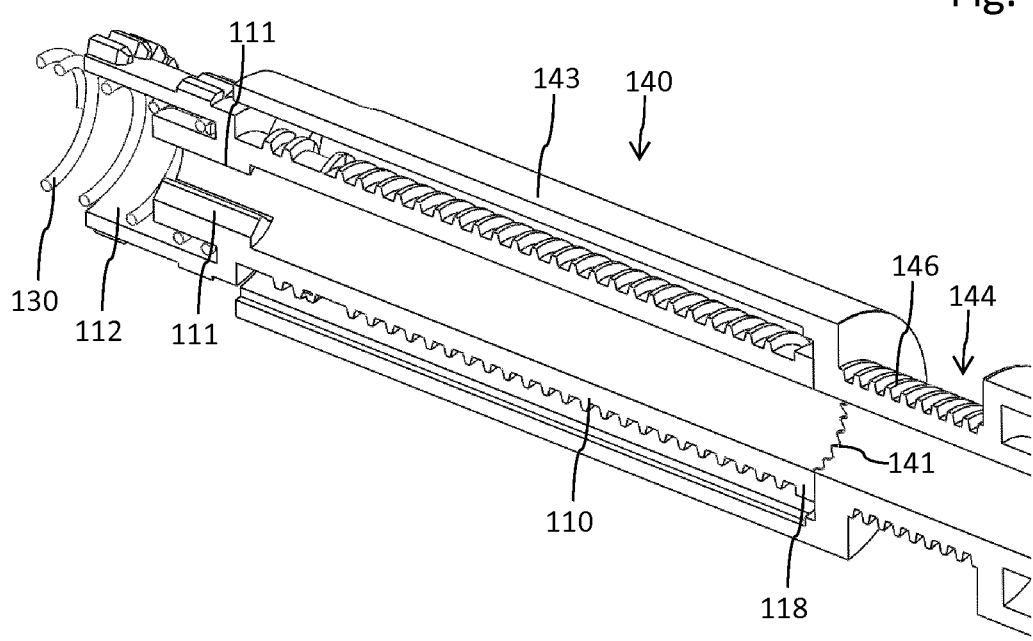
FIG. 17 is a perspective cross-sectional view of the interface of dial sleeve and drive sleeve.

The piston rod 90 further comprises at least one, typically at least two diametrically oppositely located longitudinal grooves 94 by way of which the piston rod 90 is in permanent rotational engagement with a drive sleeve 110. As shown in FIG. 17 the drive sleeve 110 comprises two radially inwardly extending protrusions 111 extending in longitudinal or axial direction from its radially inwardly-facing sidewall portion. These protrusions 111 engage with the longitudinally extending grooves 94 of the piston rod 90, that are indicated on FIG. 2.

In this way the drive sleeve 110 is permanently rotatably coupled with the piston rod 90. The drive sleeve 110, which is slidably displaceable relative to the housing 60 as well as relative to the piston rod 90 is biased relative to the housing 60 in axial direction 4 by way of a dispensing spring 130. The dispensing spring 130 is received in an annular recess 112 provided at the distal front face of the drive sleeve 110. The annular recess 112 is adapted to receive a proximal end of the dispensing spring 130 while a distal end of the dispensing spring 130 axially abuts with the support 64 centrally located inside the housing 60. The dispensing spring 130 serves to displace the drive sleeve 110 into the proximal direction 2. Hence, the drive sleeve 110 is displaceable in distal direction 1 against the action of the dispensing spring 130.

Figure 14:
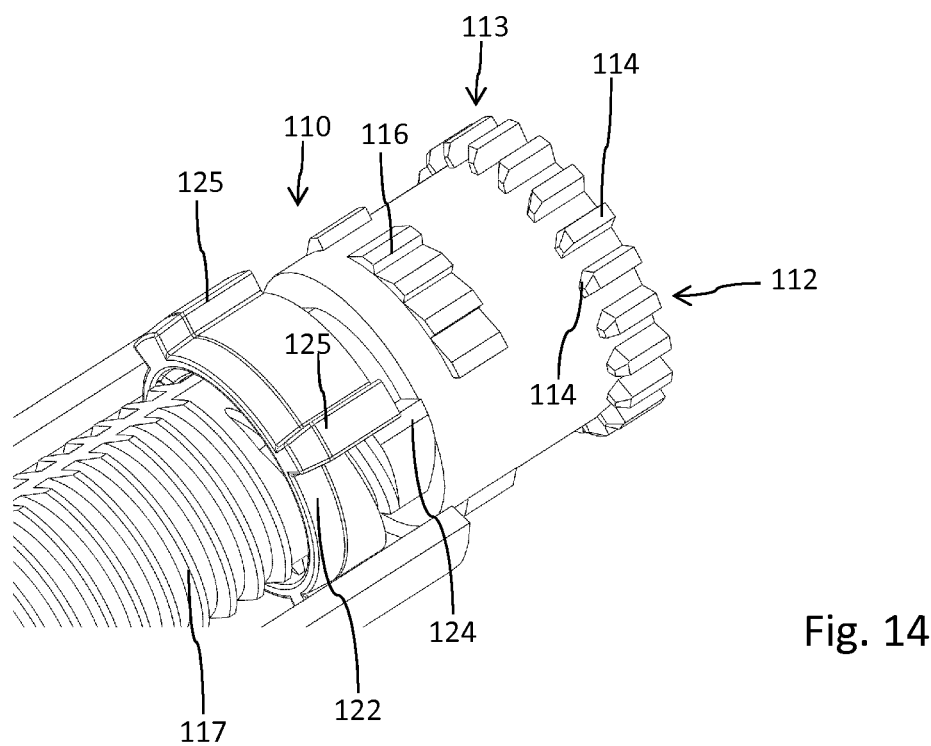

As shown in FIGS. 14 and 17 the drive sleeve 110 further comprises a geared section 113 at its distal end featuring numerous detents 114 extending radially outwardly from the outer circumference of the drive sleeve 110. At an axial distance from the geared section 113 there is provided a gear structure 116 extending around the outer circumference of the drive sleeve 110. Even further separated from the distal end the drive sleeve 110 comprises a threaded section 117 which in distal direction 2 is terminated by a radially outwardly and axially extending stop member 124.

On the threaded section 117 there is located a last dose limiting member 122 forming a last dose limiting mechanism 120. The last dose limiting member 122 may comprise an annular or ring-like shape and has a radially inwardly-facing thread engaging with the outer threaded section 117 of the drive sleeve 110. The last dose limiting member 122 comprises two or even more radially outwardly extending protrusions 125 that extend in axial direction 4. The protrusions 125 engage with a longitudinal recess or groove 142 of a dial sleeve 140.

The dial sleeve 140 comprises a radially widened distal portion 143, a neck portion 144 proximally adjacent thereto and a proximal portion 145 extending all the way through and towards the proximal end of the housing 60. The distal portion 143 of the dial sleeve 140 receives the drive sleeve 110 through which the piston rod 90 completely extends. A proximal portion of the piston rod 90 extending in proximal direction 2 from the proximal end of the drive sleeve 110 extends into or even through the neck portion 144 of the dial sleeve 140 as illustrated in FIG. 3.

In the neck portion 144 the dial sleeve 140 comprises a threaded section 146 which is threadedly engaged with a single dose limiting member 150. The single dose limiting member 150 as shown in FIGS. 3 and 4 comprises a radially inwardly-facing threaded section 152 threadedly engaged with the threaded section 146 of the dial sleeve 140. Radially outwardly the single dose limiting member 150 comprises a radially outwardly extending protrusion 154 that is rotatably constrained but axially guided in a groove 81 of an insert 80 that is permanently fixed and received in the housing 60. The groove 81 extends in axial direction 4 so that a rotation of the dial sleeve 140 relative to the housing 60 leads to an axial displacement of the single dose limiting member 150.

The drive mechanism 18 further comprises a dose setting member 100 located at a proximal end of the housing 60. The dose setting member 100 has the form of a user-actuatable dial grip and is rotatably supported on the housing 60. As illustrated in FIG. 5 the dose setting member 100 may even serve as a proximal extension of the housing 60. Near its distal end the dose setting member comprises a radially inwardly extending protrusion 102 engaging with a correspondingly-shaped recess at the housing's 60 proximal end. In this way, the dose setting member is axially constrained and axially secured to the housing 60.

At the very proximal end of the injection device 10 there is provided a dose button 105. The dose button 105 is rotatably fixed to the dose setting member, e.g. by way of a splined interface, providing a rotational coupling of dose setting member 100 and dose button 105 but allows for an axial displacement of the dose button 105 relative to the dose setting member 100 and hence relative to the housing 60. In a central portion of an end face 106 the dose button 105 comprises a distally-extending bulged portion 107 which is in permanent and direct abutment with a proximal end face of a ring gear 160. The ring gear 160 comprises a cup-shaped central receptacle to receive a proximal end of the dial sleeve 140. The ring gear 160 is permanently rotatably and axially connected to the dial sleeve 140. A rotation of the ring gear 160 as well as any axial displacement of the ring gear 160 equally transfers to the dial sleeve 140.

The ring gear 160 is selectively rotatably engageable with the dose setting member 100. As indicated in FIG. 5, the ring gear 160 comprises a geared section 162 at its outer circumference that engages with a radially inwardly extending detent structure or with a correspondingly geared or toothed structure 101 of the dose setting member 100. In this way, any rotation of the dose setting member 100 relative to the housing 60 can be equally transferred to a respective rotation of the ring gear 160. The ring gear 160 further comprises a radially-widened portion 163 at its distal end that comprises an annular geared structure 164 at an inside-facing sidewall portion.

The radially widened portion 163 the geared structure 164 meshes with a planet gear 170 that is rotatably arranged on a bearing 72 of the inlay 70. Hence, the planet gear 170 is fixed to the inlay 70 and hence fixed to the housing 60 but is rotatable with respect to the bearing 72 extending in axial direction 4. The planet gear 170 further meshes with a geared section 38 of an axially-extending shaft 37 of a first display member 22 of a display arrangement 20. The display arrangement 20 comprises a first sleeve-like or annular-shaped display member 22 as well as a second sleeve shaped and annular display member 24. The second display member 24 is arranged axially adjacent to the first display member 22. First and second display members 22, 24 comprise a display surface 28 that is provided with various consecutive symbols 29 by way of which a two or three digit number representing the size of the dose can be illustrated in the window 62 of the housing 60.

As will be explained later first and second display members 22, 24 are mutually coupled by means of a coupling member 26. The coupling member 26 comprises an axially-extending shaft 40 that is rotatably supported in a corresponding bearing of the insert 80. In this way, the coupling member 26 is free to rotate with regard to the insert 80 and hence with regard to the housing 60 but is fixed in axial direction 4. As it is apparent from FIG. 5, the proximal end of the coupling member 26 is axially constrained by a flange-like and radially outwardly extending body 23 of the first display member 22, which body 23 radially extends between the annular display surface 28 and the radially inwardly located shaft 37 of the first display member 22.

The first display member 22 is permanently rotatably engaged with the dial sleeve 140. When the dial sleeve 140 during dose setting is dialed in a dose incrementing direction 5 the first display member 22 and, depending on the size of dose and depending on the number of revolutions of the dose setting member 100, also the second display member 24 starts to rotate in order to visualize consecutive rising numbers in the window 62 that represent the size of the dose actually set. During a dose dispensing procedure, which is to be triggered by a distally-directed depression of the dose button 105 the dial sleeve 140 is disconnected or disengaged from the dose setting member 100. During dose dispensing the dial sleeve 140 together with the drive sleeve 110 rotates in an opposite dose decrementing direction 6 according to which the display arrangement 20 with its first and second display members 22, 24 returns into an initial configuration.

In the following setting of a dose will be described.

In an initial configuration as illustrated in FIG. 3 the dispensing spring 130 applies proximally-directed pressure to the drive sleeve 110 and further onto the dial sleeve 140. Since the proximal end of the dial sleeve 140 is received in a receptacle of the ring gear 160 also the ring gear 160 is located in a proximal end position. Due to the axial abutment of the ring gear 160 with the dose button 105 also the dose button 105 is in an inactive and proximal initial position.

In this configuration as it is shown in an enlarged view in FIG. 5 the toothed structure 101 of the dose setting member 100 is engaged with the geared section 162 of the ring gear 160. A rotation of the dose setting member 100 in a dose incrementing direction 5 therefore leads to a respective rotation of the dial sleeve 140. As a consequence, the single dose limiting member 150 travels in axial, presently in distal direction 1 as it becomes apparent from a comparison of FIGS. 3 and 4. The dial sleeve 140 comprises a distal stop 147 as well as a proximal stop 148 to engage with a respective stop 156 of the single dose limiting member 150. Hence, when a maximum allowable dose is set, the single dose limiting member 150 has traveled all the way in distal direction 1 until it engages with its stop 156 with a corresponding distal stop 147 of the dial sleeve 140. Mutually corresponding stops 147, 148, 156 of the dial sleeve 140 and of the single dose limiting member 150 typically extend in axial and radial direction so that a well-defined and directly acting stop can be provided as soon as a predefined angular position of the dial sleeve 140 has been reached.

In the initial configuration of the drive mechanism 18 as shown in FIG. 3, the single dose limiting member 150 is in engagement with the zero dose stop 148. In this stop configuration a rotation of the dial sleeve 140 in dose decrementing direction 6 is interrupted and prevented. So in the initial configuration of the drive mechanism 18 a dialing of the dose setting member 100 in a dose decrementing direction 6, that would lead to a negative dose size is effectively prevented. Moreover, the zero dose stop configuration also limits the dispensing procedure and serves to terminate the dispensing procedure of a dose previously set.

As the dial sleeve 140 is rotated in dose incrementing direction 5 it serves to rotate a collar 180. The collar 180 comprises numerous proximally-extending wings that are received in correspondingly-shaped axially extending recesses 149 provided at a distal end of the dial sleeve 140. The collar 180 is axially fixed but rotatable to the housing 60. Due to the mutual engagement of the wings 181 with the recesses 149 the collar 180 is permanently rotatably coupled with the dial sleeve 140. Since the recesses 149 and the wings 181 extend in axial direction 4, the dial sleeve 140 is axially displaceable relative to the collar 180 and remains rotatably coupled therewith.

The collar 180 is connected with a distal end of a helical drive spring 136 extending around the outer circumference of the dial sleeve 140. A proximal end of the helical drive spring 136 is fixed to the insert 80. Typically, in an initial configuration as shown in FIG. 3 the drive spring 136 is already pre-loaded. Upon rotation of the dial sleeve 140 in dose incrementing direction 5 the drive spring 136 is biased and wound-up further so as to increase the mechanical energy stored in the drive spring 136. In the initial or dose setting configuration the drive sleeve 110 is engaged via its distally-located geared section 113 with a correspondingly-shaped geared section 67 of the housing 60.

Hence, in the initial or dose setting configuration the drive sleeve 110 is rotatably fixed to the housing 60. The collar 180 comprises a central through opening with a radially inwardly facing geared structure 182. In the dose setting configuration the geared structure 182 facing towards the outer circumference of the drive sleeve 110 is axially-located between the geared section 113 and the geared structure 116 of the distal portion of the drive sleeve 110. In this way, the collar 180 together with the dial sleeve 140 is allowed to rotate while the drive sleeve 110 is rotatably fixed to the housing 60.

Figure 15:
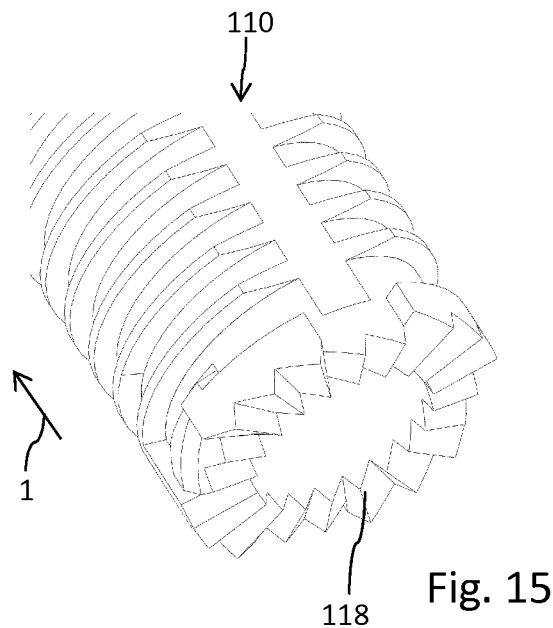
FIG. 15 shows an isolated perspective view of a proximal end of the drive sleeve.
Figure 16:
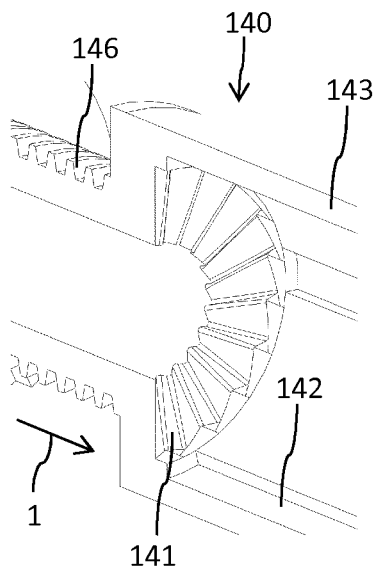
FIG. 16 shows a perspective and partially cut view of a dial sleeve to engage with the crown wheel portion of the drive sleeve according to FIG. 15.

As illustrated in FIGS. 15-17 the drive sleeve 110 comprises a crown wheel portion 118 at its distal end that meshes with a correspondingly-shaped crown wheel portion 141 of the dial sleeve 140 facing in distal direction. The teeth of the crown wheel portions 118, 141 are adapted to provide a rather smooth dose incrementing rotation of the dial sleeve 140 relative to the drive sleeve 110. The engagement of crown wheel portion 141 and 118 is designed and configured such, that the restoring torque of the biased drive spring 136 is less than a force required to rotate the dial sleeve 140 in the opposite dose decrementing direction 6 relative to the drive sleeve 110.

Since the drive sleeve 110 is axially biased by the dispensing spring 130 the drive sleeve 110 shuttles back and forth due to the axial extension of the mutually engaging crown wheel portions 118, 141 as the dial sleeve 140 is rotated in the dose incrementing direction 5 or dose decrementing direction 6. The mutual engagement of the crown wheel portions 141, 118 does not only keep the drive spring 136 biased and does not only prevent a self-actuated release of the drive spring 136 but also provides an audible as well as a tactile feedback to the user of the device during actuation, hence during dialing of the dose setting member 100. The shape and geometry of the mutually engaging crown wheel portions 118, 141 is selected such, that the dial sleeve 140 can be also rotated in a dose decrementing direction 6 in case that a selected dose should be too large.

Figure 12:
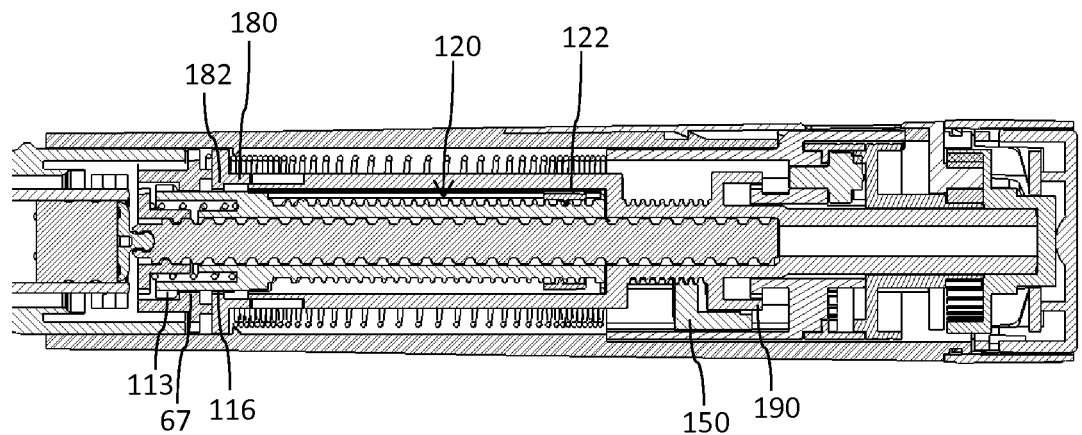
FIG. 12 is indicative of the drive mechanism according to FIG. 11 with the dose button completely depressed to trigger the dispensing procedure.

During setting of a dose and during rotation of the dial sleeve 140 relative to the drive sleeve 110 also the last dose limiting member 122 advances from its initial proximally-located position in distal direction 1 as it is apparent from a comparison of the configurations according to FIGS. 3 and 12. Since the dial sleeve 140 and the drive sleeve 110 rotate in unison during a dose dispensing procedure the last dose limiting member 122 will not be subject to any further axial displacement. During a consecutive dose setting procedure the last dose limiting member 122 will be displaced further in distal direction 1 until it engages with a radial and/or axial stop 124 provided at a distal end of the drive sleeve 110. This mutual abutment serves to prevent to dial and to select a dose that would exceed the amount of medicament left in the cartridge.

During a dose setting procedure but also during dose dispensing the ring gear 160 is permanently engaged with the dial sleeve 140 as well as with the planet gear 170. A rotation in dose incrementing direction 5, typically during dose dispensing and induced via a user dialing the dose setting member 100 relative to the housing 60 transfers into a rotation of the first display member 22 as shown in the sequence of FIG. 6a-8b. On the outer circumference of the disc- or sleeve-shaped first display member 22 there is provided a display surface 28 on which consecutive numbers ranging from 0-9 are equidistantly located.

The first display member 22 comprises an axially extending shaft 37 in a central portion. The rather smooth and even-shaped shaft 37 is intersected by the proximal portion 145 of the dial sleeve 140. In this way, the first display member 22 is rotatably supported on the dial sleeve 140. Axially adjacent to the first display member 22 there is located the second display member 24, which comprises also numerous digits ranging from 0-12. While the first display member 22 represents the ones of a two or three digit number the second display member 24 represents the tenth or decades of a two or three digit number. In this way, every discrete dose size between 0-120 IU can be illustrated by the display arrangement 20. The display arrangement 20 is by no way limited to the illustration of dose sizes between 0 and 120 but may be used also for other scales and other medicaments.

The display surfaces 28 of first and second display members 22, 24 are axially flush. First and second display members 22, 24 that constitute an odometer-like display arrangement 20 are coupled by means of a coupling member 26 featuring various geared sections 42, 44 and a retaining section 46 as it becomes apparent from FIGS. 9 and 10. The coupling member 26 is located radially offset and is hence rotatable relative to a coupling axis 7 extending parallel but radially offset from the centrally-located rotation axis 3.

Figure 10:
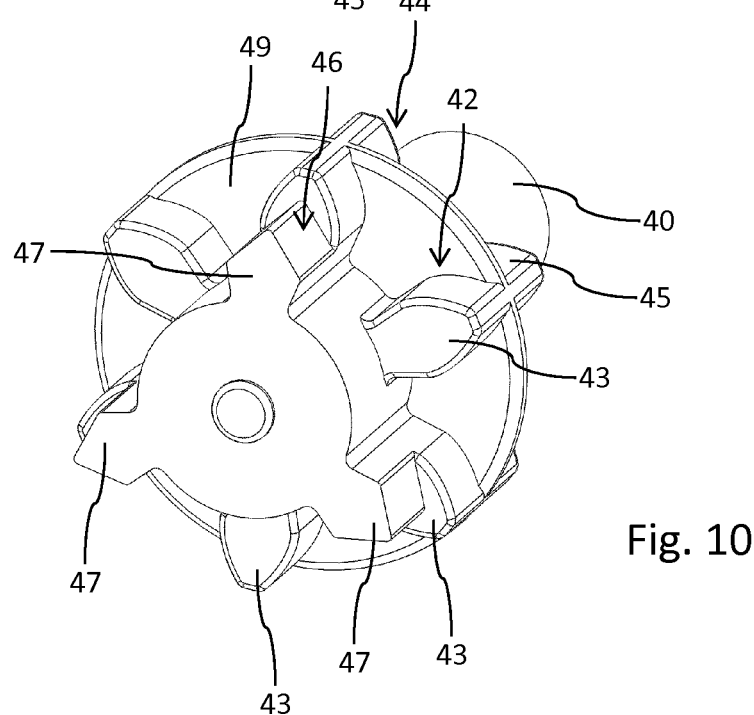
FIG. 10 shows an opposite perspective view of a proximal end of the coupling member.

The first display member 22 comprises an axially extending cam 32 near its outer edge or outer circumference. Hence, the cam 32 is located eccentric with regard to the rotation axis 3 or with regard to the center or shaft 37 of the first display member 22. The cam 32 is configured to mesh with a first geared section 42 of the coupling member 26. As illustrated in FIG. 10, the first geared section 42 comprises numerous equidistantly arranged radially outwardly extending first teeth 43. Every time the cam 32 reaches and passes by the coupling member 26, the cam 32 circumferentially or tangentially abuts and engages with one of the first teeth 43 of the first geared section 42, thereby inducing a well-defined and limited rotation onto the coupling member 26.

The coupling member 26 further comprises a second geared section 44 with a number of second teeth 45. The second geared section 44 is located axially offset and at an axial distance from the first geared section 42. As illustrated in FIG. 5, the second geared section 44 meshes with a radially inwardly-facing geared section 25 of the second display member 24, which is configured as a sleeve and which is rotatably supported by the insert 80. In this way any rotation of the coupling member 26 induced by the cam 32 of the first display member 22 is transferred into a respective rotation of the second display member 24 for each direction of rotation.

Figure 6A:
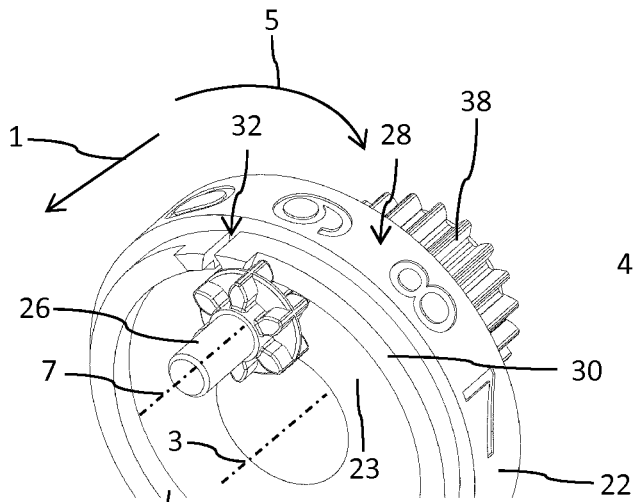
FIG. 6a is a perspective view of the first display member and the coupling member prior to an engagement of cam and coupling member.
Figure 7A:
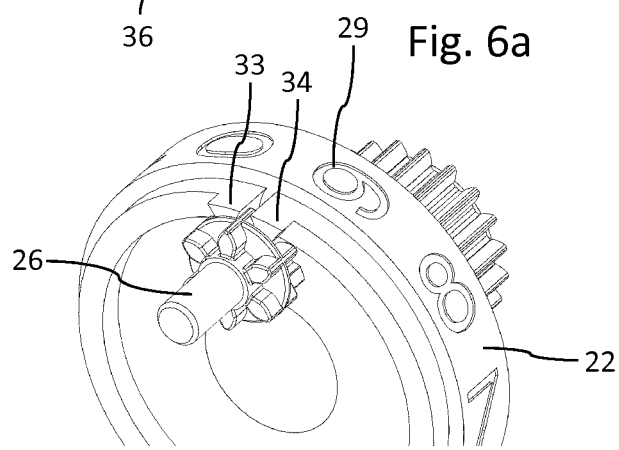
FIG. 7a shows the first display member and the coupling member according to FIG. 6a but with the cam in engagement with the coupling member.
Figure 8A:
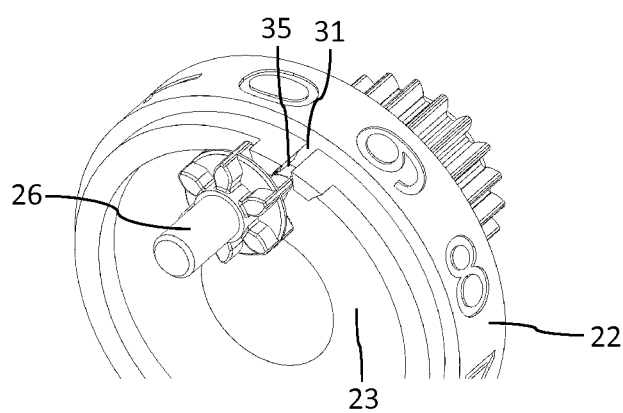
FIG. 8b shows a cross-section corresponding to the configuration according to FIG. 8a, FIG. 9 shows an isolated perspective view of the distal end of the coupling member.

The cam 32 of the first display member 22 axially extends from a retaining ring 30 extending around the entire circumference of the first display member 22. As illustrated in FIGS. 6a, 7a and 8a the retaining ring 30 is radially inwardly stepped down compared to the display surface 28.

As shown in FIG. 5, a proximal portion of the sleeve-shaped second display member 24 can be radially supported by the retaining ring 30. In this way, the first display member 22 provides a kind of bearing for the second display member 24. The retaining ring from which the cam 32 extends in distal direction 1 comprises a radially inward-facing inner surface 36 that engages and/or abuts with a retaining section 46 of the coupling member 26. The retaining ring 30 of the first display member 22 and the retaining section 46 of the coupling member 26 constitute and form a retaining arrangement 48 that serves to prevent a rotation of the coupling member 26 and hence of the second display member 24 when the cam 32 is disengaged from the coupling member 26.

Hence, the cam 32 is in engagement with the coupling member 26 only when located in a predefined angular position or when located in a predefined angular range. When located outside the predefined angular position or angular range, hence when the cam 32 is decoupled and contactless with regard to the coupling member 26 the retaining arrangement 48 serves to prevent a self-actuated or otherwise unintentional rotation of the coupling member 26 and of the second display member 24. Hence the predefined angular position or angular range is defined by the operable engagement between cam 32 and coupling member 26.

Figure 6B:
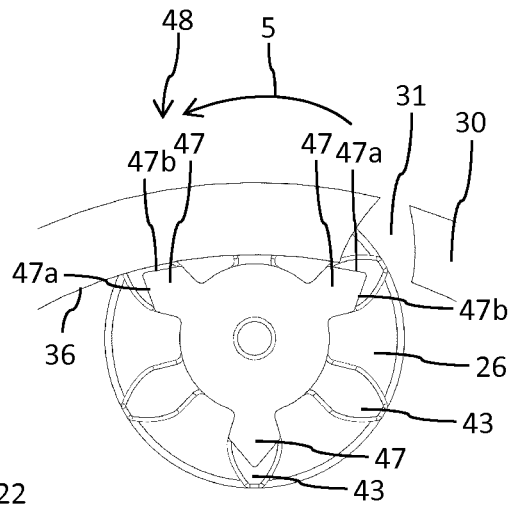
FIG. 6b shows a corresponding cross-section through the first display member as seen in distal direction.
Figure 7B:
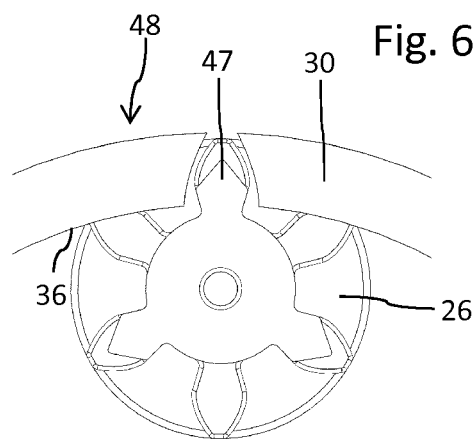
FIG. 7b is a cross-section through the first display member according to FIG. 7a, FIG. 8a shows a perspective view of the first display member and the coupling member after the cam has passed the coupling member
Figure 8B:
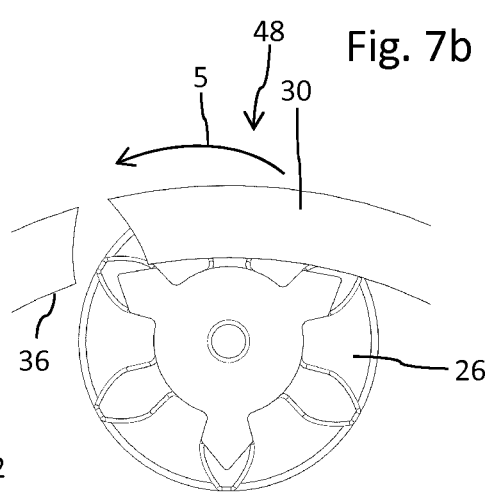

The retaining section 46 of the coupling member 26 comprises three equidistantly separated retaining teeth 47. As shown in FIG. 10, there are provided three retaining teeth while the first geared section 42 comprises six first teeth 43. As shown in FIG. 10, every second tooth of the first teeth 43 is axially adjacent with a retaining tooth 47. The retaining teeth 47 however comprise a shorter extension in radial direction compared to the first teeth 43. In addition and as illustrated in the sequence of FIGS. 6b, 7b and 8b the retaining teeth 47 comprise beveled side flanks 47a, 47b. The side flanks 47a, 47b are oriented and configured such, that the side flank 47b of a selected retaining tooth 47 as well as a side flank 47a of a neighboring retaining tooth 47 are simultaneously in radial abutment with the radially inward-facing inner surface 36 of the retaining ring 30. Due to the simultaneously abutment of two retaining teeth 47 with the retaining ring 30 the coupling member 26 is hindered from rotating while the retaining ring 30 and the first display member 22 are still free to rotate in such a way that the inner surface 36 of the retaining ring 30 slides along the side flanks 47a, 47b of neighboring retaining teeth 47.

As it is particularly apparent from FIG. 6b the retaining ring 30 comprises a radial recess 31 that is adapted to radially receive the retaining tooth 47. Apparently, the recess 31 coincides with the cam 32. Hence, when the cam 32 passes or engages with one of the first teeth 43 the retaining tooth 47 axially adjacent to the particular one of the first teeth 43 is allowed to enter the recess 31 as illustrated in FIG. 7b. As the retaining ring 30 with the cam 32 and with the first display member 22 rotates further the retaining tooth 47 leaves the recess 31 so that it engages with its side flank 47b with the retaining ring 30.

As it is further apparent from the perspective illustration of the first display member 22 according to FIGS. 6a, 7a and 8a the recess 31 extends into the cam 32 and divides the cam 32 into two cam segments 33, 34. The cam segments 33, 34 are designed and configured to fit into the intermediate space provided between two consecutive first teeth 43 of the first geared section.

In this way, the driving torque to rotate the coupling member 26 can be divided among several first teeth 43 of the first geared section. The recess 32 of the retaining ring 30 extends in axial direction 4 and extends between and separates the cam segments 32. In the region between the cam segments 33, 34 the recess 31 may comprise or form a cam slit 35 as shown in FIG. 8a.

Figure 9:
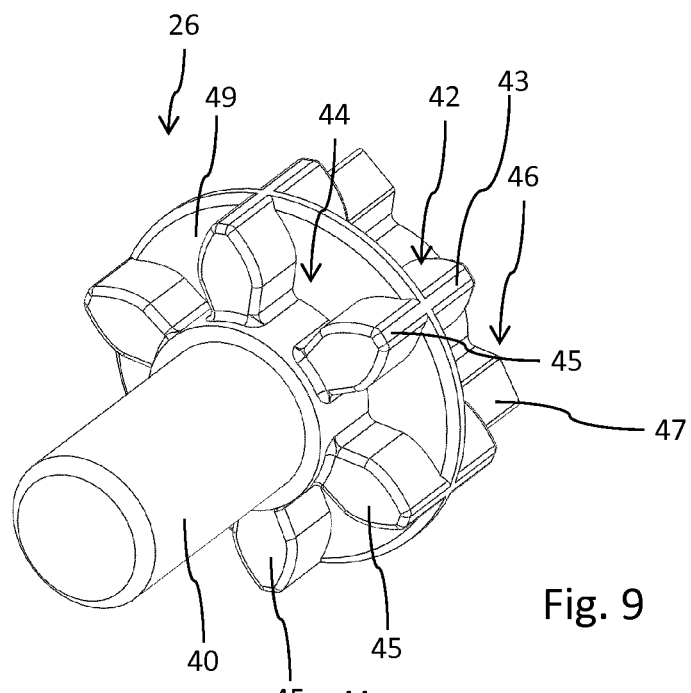

As it is further apparent from FIGS. 9 and 10 the coupling member 26 comprises a separating disc portion 49 extending between first and second geared section 42, 44. In general since the teeth 43, 45 of first and second geared section 42, 44 are flush in axial direction 4 such a separating disc portion is substantially ineffective in regard to a coupling between first and second display members 22, 24. The separating disc portion 49 may be beneficial to provide axial abutment e.g. for the second display member's 24 geared section 25.

Since the first display member 22 is permanently rotatably engaged with the dial sleeve 140 and since the cam 32 has a symmetrical shape with regard to a dose incrementing direction 5 and in regard to a dose decrementing direction 6 the odometer-like display arrangement 20 is equally operable during dose setting as well as during dose dispensing. Typically, during dose setting a sequence of increasing numbers shows up in the window 62 while during dose dispensing the numbers decrement.

In the following dispensing of a dose will be described.

Figure 11:
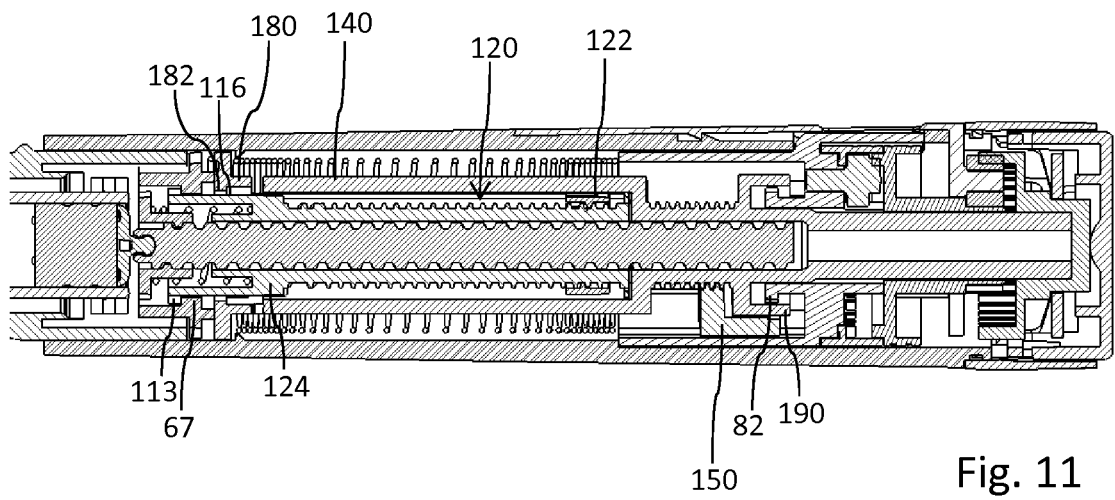
FIG. 11 shows the drive mechanism in longitudinal cross-section with the dose button partially depressed.

For dispensing of a dose the user simply depresses the dose button 105 in distal direction 1. In this way and due to the axial abutment between the dose button 105, the ring gear 160 and the dial sleeve 140, the dial sleeve 140 is displaced in distal direction 1 in unison with the drive sleeve 110, which axially abuts with the dial sleeve 140. As the ring gear 160 is displaced in distal direction 1 its geared section 162 disengages from the toothed structure 101 of the dose setting member 100 as it is illustrated in FIG. 11. There, the drive mechanism 18 is illustrated with the dose button 105 partially depressed.

As a consequence, the ring gear 160 and hence the display arrangement 20 with its first display member 22 is decoupled from the dose setting member 100. Any further rotation of the dose setting member 100 therefore no longer has an influence on the angular position of the dial sleeve 140. With the dose button 105 at least partially depressed as illustrated in FIG. 11 a further manipulation of the dose size is prevented. Moreover, the display arrangement 20 which remains engaged with the ring gear 160 is decoupled from the dose setting member 100. In the partially depressed configuration the drive sleeve 110 is displaced in distal direction to such an extent that the radially inwardly-facing geared structure 182 of the collar 180 engages with the geared structure 116 of the drive sleeve 110.

In the partially depressed configuration the drive sleeve 110, in particular its distally-located geared section 113 is still engaged and coupled with the geared section 67 of the housing 60. The drive sleeve 110 is still hindered from rotating relative to the housing 60 but is already rotatably engaged with the collar 180 that is drivable by the wound-up drive spring 136. In the course of depressing the dose button 105 in distal direction 1 a rotational coupling between the collar 180 and the drive sleeve 110 is established and activated before the drive sleeve 110 is liberated or decoupled from the housing 60. In this way uncontrolled slip of the drive sleeve 110 can be effectively prevented.

As the dose button 105 is completely depressed in distal direction the geared section 113 with its various detents 114 of the drive sleeve 110 disengage from the geared section 67 of the housing 60 so the drive sleeve 110 is no longer rotationally constrained. Torque and mechanical energy stored in the drive spring 136 is then transmitted through the collar 180 to the drive sleeve 110 causing it to rotate. A rotating drive sleeve 110 leads to a respective rotation of the piston rod 90, which due to its threaded engagement with the housing 60 advances in distal direction so as to expel a predefined amount of the medicament 11 from the cartridge 12.

During the dispensing procedure the dial sleeve 140 also rotates in the dose decrementing direction 6. The single dose limiting member 150 returns into its initial configuration as shown in FIG. 3 until it engages with a corresponding stop 148 of the dial sleeve. Simultaneously, the rotation of the ring gear 160 causes the first display member 22 to rotate back towards a zero unit position.

Figure 13:
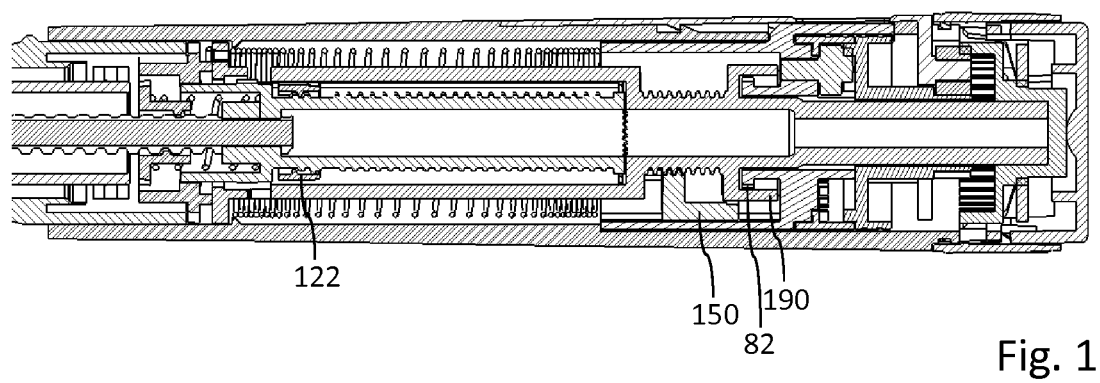
FIG. 13 is illustrative of the drive mechanism according to FIGS. 11 and 12 with the dose button released prior to a termination of the dose dispensing, FIG. 14 perspectively illustrates a distal end of the drive sleeve threadedly engaged with a last dose member.

Alternatively, a dispensing procedure may be abruptly stopped when the user releases the dose button 105 as it is illustrated in FIG. 13. Then, under the action of the dispensing spring 130 the drive sleeve 110 will first re-engage with the housing's 60 geared section 67 and will then disengage and release from the collar 180.

When the drive sleeve 110 returns into its initial position under the action of the dispensing spring 130, the chamfers or beveled portions 115 provided on a proximal end of the detents 114 of the drive sleeve's 110 geared section 113 serve to induce a slight counter-directed rotation of the drive sleeve 110. Due to this small but distinct counter-rotation the piston rod 90 will be retracted by a predefined distance. This backs the pressure piece 92 away from the piston 14 of the cartridge 12 so that the piston 14 may elastically relax into an initial configuration in proximal direction 2 so that inevitable relaxing of the elastic piston 14 has no or at least a reduced pressure increasing effect on the medicament 11 contained in the cartridge 12. In this way, post dispensing droplet generation to be observed at the distal tip of the needle can be effectively reduced.

In order to provide an audible feedback during dose dispensing and in order to indicate to a user that a dispensing procedure is in progress the drive mechanism 18 and the injection device 10 comprise a clicking member 190 that is audibly engaged with a toothed structure 82 of the insert 80 during dose dispensing but which is disengaged and decoupled from the toothed structure 82 when the drive mechanism 18 is in dose setting configuration. The clicking member 190 comprises an arched shape and is provided at a proximal end of a cup-shaped and radially widened receptacle 139 on the proximal portion 145 of the dial sleeve 140. The receptacle 139, radially confined by a rim shaped side wall portion 138, opens towards the proximal end is adapted to receive a circumferential or ring-shape toothed structure 82 of the insert 80, which is fixed to the housing 60.

Figure 18:
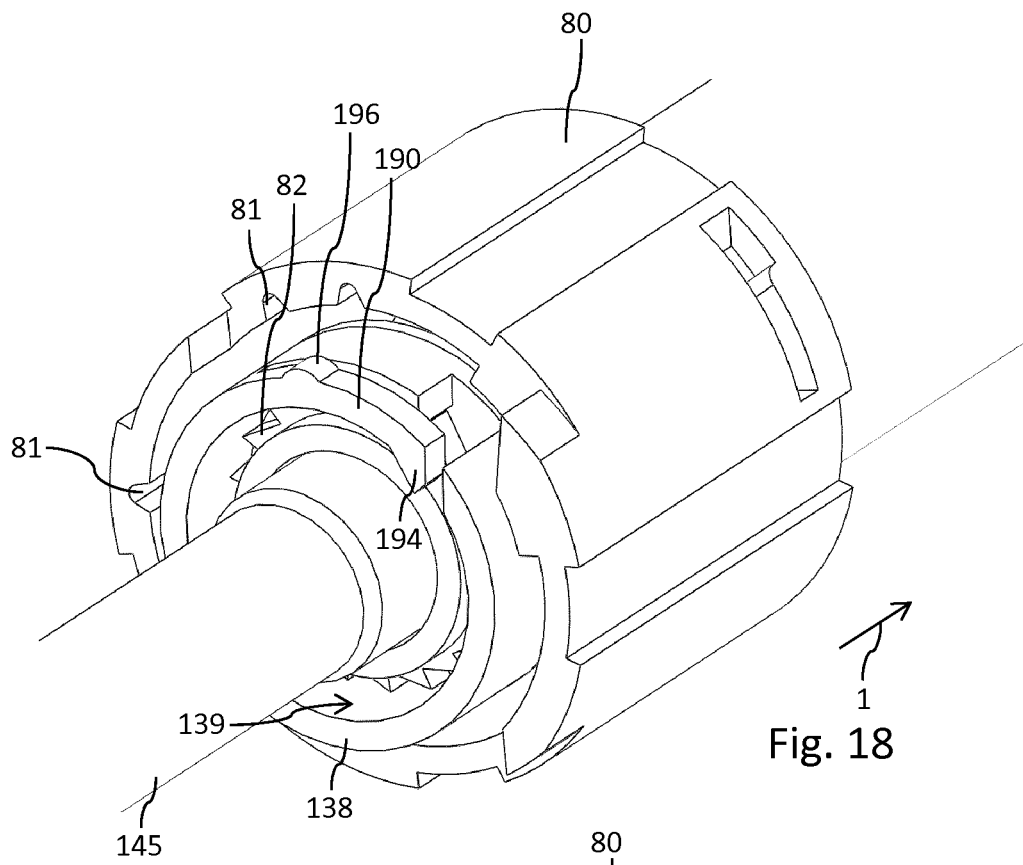
FIG. 18 is a perspective illustration of a dispense clicking mechanism during dose setting.
Figure 19:
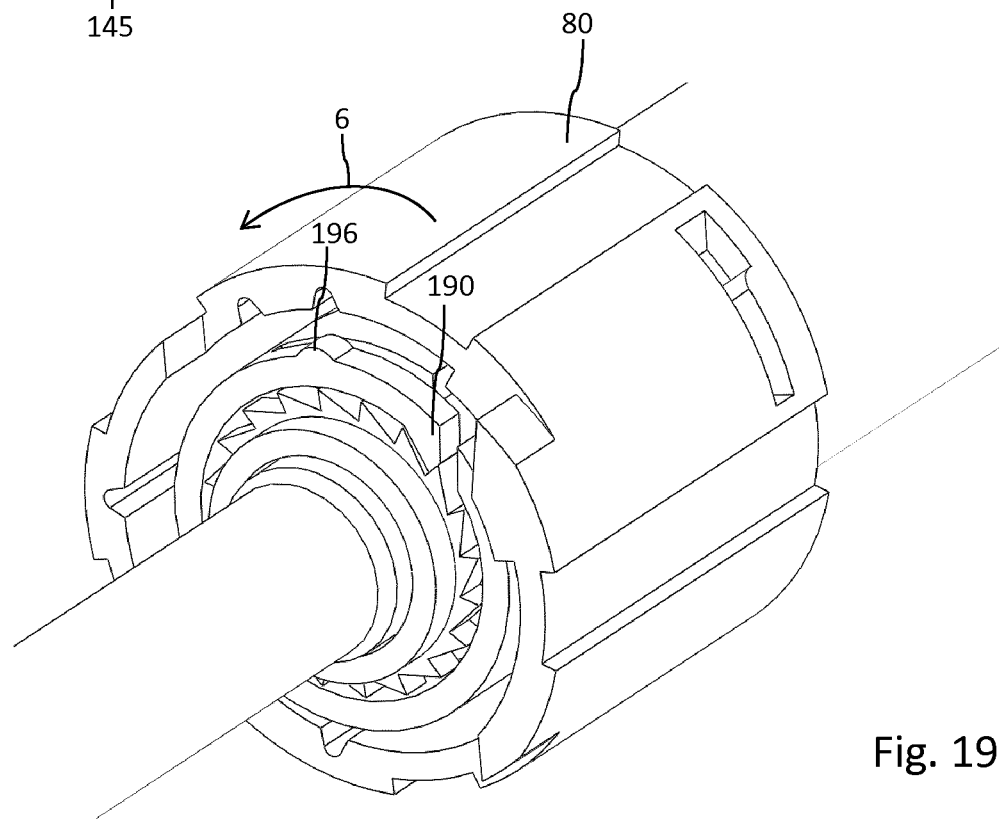
FIG. 19 shows the dispense clicking mechanism according to FIG. 18 during dose dispensing and FIG. 20 shows a cross-section through the dispense clicking mechanism according to FIGS. 18 and 19.
Figure 20:
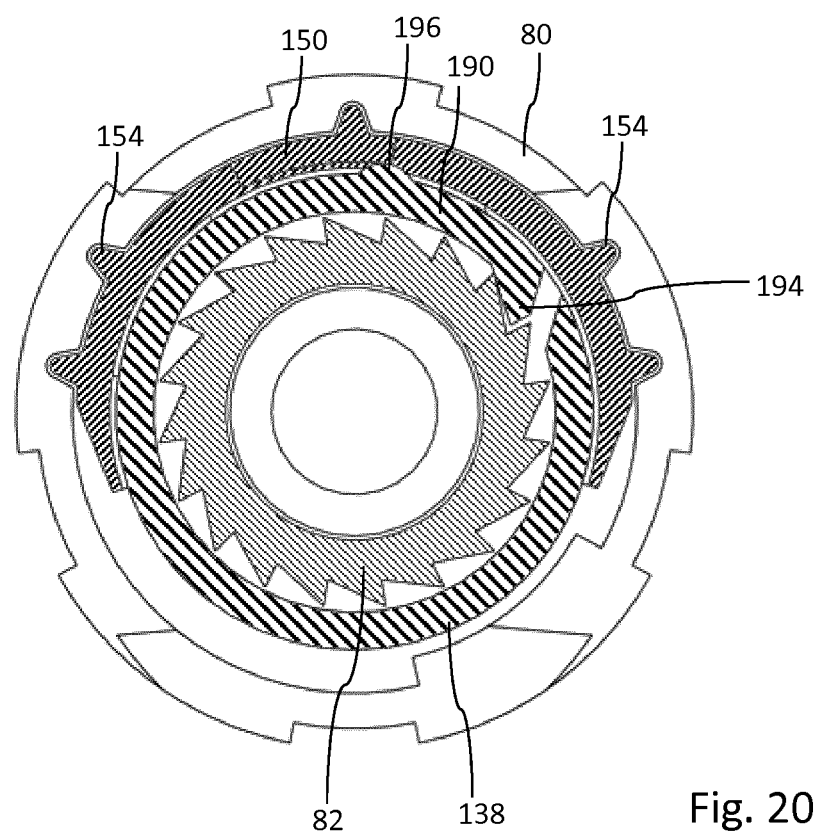

As shown in FIGS. 3 and 18 the clicking member 190 and the toothed structure 82 are axially offset. It is due to the distally-directed displacement of the dial sleeve 140 during a dose dispensing procedure that the clicking member 190 engages and meshes with the toothed structure 82 as it is apparent from FIGS. 12 and 19. As the dial sleeve 140 rotates in dose decrementing direction 6 the clicking member 190 repeatedly meshes and slides along consecutive teeth of the insert's 80 toothed structure 82. With every tooth an audible click sound is generated indicating to the user, that dose dispensing is still in progress.

The clicking member 190 comprises a radially inwardly extending nose portion 194 matching in shape and geometry with the shape of the saw tooth-like shaped toothed structure 82.

At a predefined tangential or circumferential distance from the free end of the clicking member 190, where the nose portion 194 is provided the clicking member 190 comprises a radially outwardly extending bulged portion 196. The bulged portion 196 extends slightly radially outwardly compared to tangentially adjacent and rather smooth and arc-shaped portions of the clicking member 190. As the end of the dispensing procedure approaches, which coincides with a returning of the single dose limiting member 150 into its proximal end position as indicated in FIG. 3, the single dose limiting member 150 engages with the bulged portion 196 and applies a radially inwardly-directed tension or pre-tension onto the clicking member 190.

In this way, the flexible length of the clicking member 190 is effectively shortened and the clicking member, hence its arc-shaped clicking arm is stiffened. As a zero dose configuration is finally reached that coincides with a termination of the dispensing procedure a more energetic click sound is generated, thereby audibly indicating to a user, that the end of the dispensing procedure has been reached.

Release of the dose button 105 and the corresponding proximally-directed displacement of the dial sleeve 140 disengages the clicking member 190 from the toothed structure. In order to allow elastic relaxation of the clicking member the single dose limiting member 150 comprises an annular recess 158 providing a radially outwardly located relaxing space for the clicking member 190. In this way, a permanent deformation of the clicking member 190 can be prevented to counteract rupture of the clicking member's material due to creep.

LIST OF REFERENCE NUMBERS 1 distal direction
2 proximal direction
3 rotation axis
4 axial direction
5 dose incrementing direction
6 dose decrementing direction
7 coupling axis
10 injection device
11 medicament
12 cartridge
13 cartridge holder
14 piston
16 socket
18 drive mechanism
19 protective cap
20 display arrangement
22 first display member
23 body
24 second display member
25 geared section
26 coupling member
28 display surface
29 symbol
30 retaining ring
31 recess
32 cam
33 cam segment
34 cam segment
35 cam slit
36 inner surface
37 shaft
38 geared section
40 shaft
42 first geared section 43 tooth
44 second geared section
45 tooth
46 retaining section
47 retaining tooth
47a,b side flank
48 retaining arrangement
49 separating disc
60 housing
62 window
63 cover
64 support
65 inner thread
67 geared section
70 inlay
72 bearing
80 insert
81 groove
82 toothed structure
90 piston rod
91 outer thread
92 pressure piece
94 groove
100 dose setting member
101 toothed structure
102 protrusion
105 dose button
106 end face
107 bulged portion
110 drive sleeve
111 protrusion
112 annular recess
113 geared section
114 detent
115 beveled portion
116 geared structure
117 threaded section
118 crown wheel portion
119 stop member
120 last dose limiting mechanism
122 last dose limiting member
124 stop member
125 protrusion
130 dispensing spring
136 drive spring
138 sidewall portion
139 receptacle
140 dial sleeve
141 crown wheel portion
142 groove
143 distal portion
144 neck portion
145 proximal portion
146 threaded section
147 stop
148 stop
149 recess
150 single dose limiting member
152 threaded section
154 protrusion
156 stop
158 recess
160 ring gear
162 geared section
163 radially widened portion
164 geared structure
170 planet gear
180 collar
181 wing
182 geared structure
190 clicking member
194 nose portion
196 bulged portion

The invention claimed is:

1. A display arrangement for an injection device for displaying a size of a dose of a medicament, the display arrangement comprising:
a housing providing a rotation axis extending in an axial direction;
a first display member rotatably supported inside the housing with regard to the rotation axis and comprising at least one cam radially offset from the rotation axis;
a second display member rotatably supported inside the housing with regard to the rotation axis and arranged axially adjacent to the first display member; and
a coupling member rotatably engaged with the second display member,
wherein the at least one cam selectively engages with the coupling member, wherein the coupling member is engaged with the at least one cam of the first display member only when the first display member is in a predefined angular position or angular range,
wherein a retaining arrangement is configured to engage the coupling member with the first display member when the at least one cam of the first display member and the coupling member are disengaged, and
wherein the retaining arrangement comprises at least two retaining teeth separated in a circumferential direction on an outer circumference of the coupling member, wherein the at least two retaining teeth are in radial abutment with a retaining ring of the first display member when the first display member is outside the predefined angular position or angular range.

2. The display arrangement according to claim 1, wherein the retaining arrangement is configured to keep the coupling member in a fixed angular position while the first display member is rotatable between consecutive predefined angular positions or predefined angular ranges.

3. The display arrangement according to claim 1, wherein the coupling member is rotatably supported in the housing with regard to a coupling axis extending parallel but radially offset to the rotation axis and wherein the coupling member comprises a first geared section with a plurality of first teeth to mesh with the at least one cam when the first display member is in the predefined angular position or angular range.

4. The display arrangement according to claim 3, wherein the coupling member comprises a second geared section comprising a plurality of second teeth meshing with a geared section of the second display member.

5. The display arrangement according to claim 3, wherein the at least two retaining teeth are arranged axially offset to the plurality of first teeth of the coupling member.

6. The display arrangement according to claim 3, wherein the at least two retaining teeth are arranged axially adjacent to the plurality of first teeth of the coupling member.

7. The display arrangement according to claim 3, wherein a radial extension of the at least two retaining teeth is shorter than a radial extension of the plurality of first teeth.

8. The display arrangement according to claim 3, wherein the at least two retaining teeth are at least in sections axially flush with at least two of the plurality of first teeth.

9. The display arrangement according to claim 3, wherein the at least one cam radially overlaps with the retaining ring and axially protrudes from the retaining ring.

10. The display arrangement according to claim 3, wherein the retaining ring comprises a radially extending slit to receive one of the at least two retaining teeth when the first display member rotates through the predefined angular range or beyond the predefined angular position.

11. The display arrangement according claim 10, wherein the at least one cam comprises a first cam segment and a second cam segment separated in the circumferential direction by the slit of the retaining ring extending therebetween in the axial direction and a radial direction.

12. The display arrangement according to claim 3, wherein configurations of the retaining arrangement configured to engage the coupling member with the first display member when the at least one cam of the first display member and the coupling member are disengaged comprise configurations to engage a radially inward facing inner surface of the retaining ring.

13. The display arrangement according to claim 1, wherein at least one of the first display member and the second display member comprises a sleeve like shape and wherein at least one of the first display member and the second display member comprises a display surface with consecutive dose size indicating symbols on an outer circumference.

14. A display arrangement for an injection device for displaying a size of a dose of a medicament, the display arrangement comprising:
  a housing providing a rotation axis extending in an axial direction;
  a first display member rotatably supported inside the housing with regard to the rotation axis and comprising at least one cam radially offset from the rotation axis;
  a second display member rotatably supported inside the housing with regard to the rotation axis and arranged axially adjacent to the first display member; and
  a coupling member rotatably engaged with the second display member,
    wherein the at least one cam only selectively engages with the coupling member, wherein the coupling member is engaged with the at least one cam of the first display member only when the first display member is in a predefined angular position or angular range,
    wherein a retaining arrangement is configured to engage the coupling member with the first display member when the at least one cam of the first display member and the coupling member are disengaged,
    wherein the coupling member is rotatably supported in the housing with regard to a coupling axis extending parallel and radially offset to the rotation axis, and
  wherein the coupling member comprises a first geared section with a plurality of first teeth to mesh with the at least one cam when the first display member is in the predefined angular position or angular range.

15. A drive mechanism for an injection device for dispensing a dose of a medicament, the drive mechanism comprising:
  an elongated housing extending in an axial direction and providing a rotation axis extending in the axial direction;
  a piston rod configured to operably engage with a piston of a cartridge and further configured to displace the piston in an axial distal direction;
  a dose setting member rotatably supported on the housing;
  a drive sleeve rotatably or threadedly engaged with the piston rod; and
  a display arrangement comprising:
    a first display member rotatably supported inside the housing with regard to the rotation axis and comprising at least one cam radially offset from the rotation axis;
    a second display member rotatably supported inside the housing with regard to the rotation axis and arranged axially adjacent to the first display member; and
    a coupling member rotatably engaged with the second display member,
    wherein the at least one cam selectively engages with the coupling member, wherein the coupling member is engaged with the at least one cam of the first display member only when the first display member is in a predefined angular position or angular range,
    wherein a retaining arrangement is configured to engage the coupling member with the first display member when the at least one cam of the first display member and the coupling member are disengaged,
    wherein the display arrangement is alternately engageable with the drive sleeve and with the dose setting member for dispensing or setting of the dose of the medicament, and
    wherein the retaining arrangement comprises at least two retaining teeth separated in a circumferential direction on an outer circumference of the coupling member, wherein the at least two retaining teeth are in radial abutment with a retaining ring of the first display member when the first display member is outside the predefined angular position or angular range.

16. The drive mechanism according to claim 15, further comprising an arc-shaped clicking member configured to audibly engage with a toothed structure of the housing or of an insert attached to the housing, wherein the clicking member is elastically and radially deformable by engagement with an axially displaceable last dose limiting member.

17. An injection device for dispensing a dose of a medicament, comprising:
  an elongated housing extending in an axial direction and providing a rotation axis extending in the axial direction;
  a piston rod configured to operably engage with a piston of a cartridge and further configured to displace the piston in an axial distal direction;
  a dose setting member rotatably supported on the housing;
  a drive sleeve rotatably or threadedly engaged with the piston rod;
  a display arrangement comprising:
    a first display member rotatably supported inside the housing with regard to the rotation axis and comprising at least one cam radially offset from the rotation axis;
    a second display member rotatably supported inside the housing with regard to the rotation axis and arranged axially adjacent to the first display member; and
    a coupling member rotatably engaged with the second display member,
    wherein the at least one cam selectively engages with the coupling member, wherein the coupling member is engaged with the at least one cam of the first display member only when the first display member is in a predefined angular position or angular range,
    wherein a retaining arrangement is configured to engage the coupling member with the first display member when the at least one cam of the first display member and the coupling member are disengaged, wherein the display arrangement is alternately engageable with the drive sleeve and with the dose setting member for dispensing or setting of the dose of the medicament, and wherein the retaining arrangement comprises at least two retaining teeth separated in a circumferential direction on an outer circumference of the coupling member, wherein the at least two retaining teeth are in radial abutment with a retaining ring of the first display member when the first display member is outside the predefined angular position or angular range; and a cartridge at least partially filled with the medicament and being arranged to operably engage the piston rod.

18. The injection device according to claim 17, wherein the cartridge is arranged in the housing.

19. The injection device according to claim 17, wherein the cartridge is arranged in a cartridge holder connected or connectable to the housing.

\* \* \* \* \*

UNITED STATES PATENT AND TRADEMARK OFFICE
CERTIFICATE OF CORRECTION

PATENT NO. : 10,589,032 B2
APPLICATION NO. : 15/306133
DATED : March 17, 2020
INVENTOR(S) : Jones et al.

Page 1 of 1

It is certified that error appears in the above-identified patent and that said Letters Patent is hereby corrected as shown below:

In the Specification

In Column 1, Line 8 (approx.), delete "371of" and insert -- 371 of --

In the Claims

In Column 29, Line 9, Claim 11, after "according" insert -- to --

Signed and Sealed this
Twentieth Day of October, 2020

Andrei Iancu
*Director of the United States Patent and Trademark Office*